(12) United States Patent
Feezor et al.

(10) Patent No.: US 11,039,831 B2
(45) Date of Patent: Jun. 22, 2021

(54) SUTURE PASSER SYSTEMS AND METHODS FOR TONGUE OR OTHER TISSUE SUSPENSION AND COMPRESSION

(71) Applicant: Siesta Medical, Inc., Los Gatos, CA (US)

(72) Inventors: Christopher Feezor, San Jose, CA (US); Erik van der Burg, Los Gatos, CA (US); Peter Martin, Mountain View, CA (US); Jason van Tassel, Los Altos, CA (US)

(73) Assignee: Siesta Medical, Inc., Los Gatos, CA (US)

( * ) Notice: Subject to any disclaimer, the term of this patent is extended or adjusted under 35 U.S.C. 154(b) by 138 days.

(21) Appl. No.: 16/128,816

(22) Filed: Sep. 12, 2018

(65) Prior Publication Data

US 2019/0167264 A1    Jun. 6, 2019

Related U.S. Application Data

(63) Continuation of application No. 14/639,774, filed on Mar. 5, 2015, now abandoned.
(Continued)

(51) Int. Cl.
*A61B 17/06* (2006.01)
*A61B 17/04* (2006.01)
(Continued)

(52) U.S. Cl.
CPC .... *A61B 17/06166* (2013.01); *A61B 17/0401* (2013.01); *A61B 17/0469* (2013.01);
(Continued)

(58) Field of Classification Search
CPC ............ A61B 17/0401; A61B 17/0469; A61B 17/0482; A61B 17/0485; A61B 17/06166;
(Continued)

(56) References Cited

U.S. PATENT DOCUMENTS 2,143,910 A    1/1939   Didusch
2,167,251 A    7/1939   Rogers
(Continued)

FOREIGN PATENT DOCUMENTS

RU              108286        9/2011
WO       WO 1999/003402       1/1999
(Continued)

OTHER PUBLICATIONS

U.S. Appl. No. 16/213,079, filed Dec. 7, 2018, van der Burg et al.
(Continued)

*Primary Examiner* — Jocelin C Tanner
(74) *Attorney, Agent, or Firm* — Knobbe, Martens, Olson & Bear, LLP

(57) ABSTRACT

Suture passer systems for tissue suspension and tissue compression are described. The system can include a shaft and a needle, wherein the needle is freely rotatable with respect to the shaft. The suture may include an overmolded segment. Methods of placing one or more implants, sutures, fastener, bone anchors and other devices are also described. The methods include moving tissue, including the superior pharyngeal constrictor muscle, palatopharyngeal arch, and palatoglossal arch. The methods include hyoid bone suspension.

20 Claims, 36 Drawing Sheets

Related U.S. Application Data

(60) Provisional application No. 61/948,473, filed on Mar. 5, 2014.

(51) Int. Cl.
| | | |
|---|---|---|
| *A61B 17/064* | (2006.01) | |
| *A61B 17/24* | (2006.01) | |
| *A61B 17/00* | (2006.01) | |
| *A61F 2/00* | (2006.01) | |

(52) U.S. Cl.
CPC ...... *A61B 17/0482* (2013.01); *A61B 17/0485* (2013.01); *A61B 17/064* (2013.01); *A61B 17/24* (2013.01); *A61B 2017/00814* (2013.01); *A61B 2017/00991* (2013.01); *A61B 2017/044* (2013.01); *A61B 2017/0414* (2013.01); *A61B 2017/0496* (2013.01); *A61B 2017/061* (2013.01); *A61B 2017/06009* (2013.01); *A61B 2017/0618* (2013.01); *A61B 2017/06023* (2013.01); *A61B 2017/0641* (2013.01); *A61B 2017/06042* (2013.01); *A61B 2017/0647* (2013.01); *A61B 2017/0649* (2013.01); *A61B 2017/06176* (2013.01); *A61F 2/0059* (2013.01); *A61F 2250/0007* (2013.01)

(58) Field of Classification Search
CPC .................. A61B 17/064; A61B 17/24; A61B 2017/00814; A61B 2017/00991; A61B 2017/0414; A61B 2017/044; A61B 2017/0496; A61B 2017/06009; A61B 2017/06023; A61B 2017/06042; A61B 2017/061; A61B 2017/06176; A61B 2017/0618; A61B 2017/0641; A61B 2017/0647; A61B 2017/0649; A61F 2/0059; A61F 2250/0007
See application file for complete search history.

(56) References Cited

U.S. PATENT DOCUMENTS

| | | | |
|---|---|---|---|
| 3,194,239 A | | 7/1965 | Sullivan |
| 3,570,497 A | | 3/1971 | Lemole |
| 3,709,373 A | | 1/1973 | Aguilar |
| 4,034,763 A | | 7/1977 | Frazier |
| 4,185,626 A | | 1/1980 | Jones et al. |
| 4,372,293 A | | 2/1983 | Vijil-Rosales |
| 4,441,497 A | | 4/1984 | Paudler |
| 4,557,264 A | | 12/1985 | Hinsch |
| 4,792,336 A | | 12/1988 | Hlavacek et al. |
| 4,959,069 A | | 9/1990 | Brenann et al. |
| 5,250,055 A | | 10/1993 | Moore et al. |
| 5,330,488 A | | 7/1994 | Goldrath |
| 5,336,231 A | | 8/1994 | Adair |
| 5,337,736 A | | 8/1994 | Reddy |
| 5,364,407 A | | 11/1994 | Poll |
| 5,391,174 A | | 2/1995 | Weston |
| 5,411,523 A | | 5/1995 | Goble |
| 5,443,482 A | | 8/1995 | Stone et al. |
| 5,501,691 A | | 3/1996 | Goldrath |
| 5,534,011 A | | 7/1996 | Greene, Jr. et al. |
| 5,620,012 A | | 4/1997 | Benderev |
| 5,672,316 A | | 9/1997 | Knapp |
| 5,692,520 A | | 12/1997 | Lavoisier |
| 5,692,530 A | | 12/1997 | Bible et al. |
| 5,722,981 A | | 3/1998 | Stevens |
| 5,868,789 A | | 2/1999 | Huebner |
| 5,895,395 A | | 4/1999 | Yeung |
| 5,906,624 A | | 5/1999 | Wenstrom, Jr. |
| 5,980,559 A | | 11/1999 | Bonutti |
| 5,988,171 A | * | 11/1999 | Sohn .................. A61B 17/0401 128/848 |
| 6,096,051 A | | 8/2000 | Kortenbach et al. |
| 6,161,541 A | | 12/2000 | Woodson |
| 6,258,106 B1 | | 7/2001 | Leonard |
| 6,264,677 B1 | | 7/2001 | Simon et al. |
| 6,273,852 B1 | | 8/2001 | Lehe et al. |
| 6,368,326 B1 | | 4/2002 | Dakin |
| 6,554,845 B1 | | 4/2003 | Fleenor et al. |
| 6,610,080 B2 | | 8/2003 | Morgan |
| 6,638,283 B2 | | 10/2003 | Thal |
| 6,638,286 B1 | | 10/2003 | Burbank |
| 6,660,023 B2 | | 12/2003 | McDevitt et al. |
| 6,672,316 B2 | | 1/2004 | Weihrauch |
| 6,746,456 B2 | | 6/2004 | Xiao |
| 6,786,913 B1 | | 9/2004 | Sancoff et al. |
| 6,984,237 B2 | | 1/2006 | Hatch et al. |
| 6,991,636 B2 | | 1/2006 | Rose |
| 7,081,126 B2 | | 7/2006 | McDevitt et al. |
| 7,090,672 B2 | | 8/2006 | Underwood et al. |
| 7,213,599 B2 | | 5/2007 | Conrad et al. |
| 7,232,448 B2 | | 6/2007 | Battles |
| 7,237,554 B2 | | 7/2007 | Conrad et al. |
| 7,306,613 B2 | | 12/2007 | Kawashima et al. |
| 7,337,781 B2 | | 3/2008 | Vassallo |
| 7,367,340 B2 | | 5/2008 | Nelson et al. |
| 7,401,611 B2 | | 7/2008 | Conrad et al. |
| 7,625,386 B2 | | 12/2009 | Abe et al. |
| 7,673,635 B2 | | 3/2010 | Conrad et al. |
| 7,674,276 B2 | | 3/2010 | Stone et al. |
| 7,703,460 B2 | | 4/2010 | Conrad et al. |
| 7,867,251 B2 | | 1/2011 | Colleran et al. |
| 7,892,256 B2 | | 2/2011 | Grafton |
| 7,918,868 B2 | | 4/2011 | Marshall et al. |
| 8,038,712 B2 | | 10/2011 | van der Burg et al. |
| 8,096,303 B2 | | 1/2012 | Dineen et al. |
| 8,167,787 B2 | | 5/2012 | Gillis |
| 8,177,795 B2 | | 5/2012 | Niese et al. |
| 8,186,355 B2 | | 5/2012 | van der Burg et al. |
| 8,236,027 B2 | | 8/2012 | Wu |
| 8,460,322 B2 | | 6/2013 | van der Burg et al. |
| 8,561,616 B2 | | 10/2013 | Rousseau et al. |
| 8,561,617 B2 | | 10/2013 | Lindh et al. |
| 8,821,495 B2 | | 9/2014 | van der Burg et al. |
| 8,911,347 B2 | | 12/2014 | Browning |
| 9,386,981 B2 | | 7/2016 | van der Burg et al. |
| 9,463,014 B2 | | 10/2016 | Feezor et al. |
| 9,877,862 B2 | | 1/2018 | Weadock |
| 10,182,810 B2 | | 1/2019 | van der Burg et al. |
| 2003/0149447 A1 | | 8/2003 | Morency et al. |
| 2004/0134491 A1 | | 7/2004 | Pflueger et al. |
| 2005/0119696 A1 | | 6/2005 | Walters et al. |
| 2005/0126563 A1 | | 6/2005 | van der Burg et al. |
| 2005/0149122 A1 | | 7/2005 | McDevitt et al. |
| 2005/0192631 A1 | | 9/2005 | Grafton |
| 2005/0245932 A1 | | 11/2005 | Fanton |
| 2005/0288690 A1 | | 12/2005 | Bourque et al. |
| 2006/0070626 A1 | | 4/2006 | Frazier et al. |
| 2006/0106423 A1 | | 5/2006 | Weisel et al. |
| 2006/0150986 A1 | | 7/2006 | Roue et al. |
| 2006/0201519 A1 | | 9/2006 | Frazier et al. |
| 2006/0207606 A1 | | 9/2006 | Roue et al. |
| 2006/0207607 A1 | | 9/2006 | Hirotsuka et al. |
| 2006/0207608 A1 | | 9/2006 | Hirotsuka et al. |
| 2006/0207612 A1 | | 9/2006 | Jackson et al. |
| 2006/0235264 A1 | | 10/2006 | Vassallo |
| 2006/0271060 A1 | | 11/2006 | Gordon |
| 2006/0276817 A1 | | 12/2006 | Vassallo et al. |
| 2006/0282081 A1 | | 12/2006 | Fanton et al. |
| 2006/0282082 A1 | | 12/2006 | Fanton et al. |
| 2006/0282083 A1 | | 12/2006 | Fanton et al. |
| 2006/0282088 A1 | | 12/2006 | Ryan |
| 2007/0144539 A1 | | 6/2007 | Van Der Burg et al. |
| 2007/0149986 A1 | | 6/2007 | Morris et al. |
| 2007/0149987 A1 | | 6/2007 | Wellman et al. |
| 2007/0179509 A1 | | 8/2007 | Nagata et al. |
| 2007/0179529 A1 | | 8/2007 | Doyle |
| 2007/0213770 A1 | * | 9/2007 | Dreyfuss .......... A61B 17/06166 606/228 |
| 2007/0225763 A1 | | 9/2007 | Zwolinski et al. |
| 2007/0261701 A1 | | 11/2007 | Sanders |
| 2007/0288057 A1 | | 12/2007 | Kuhnel |

(56) References Cited

U.S. PATENT DOCUMENTS

| | | |
|---|---|---|
| 2008/0023012 A1 | 1/2008 | Dineen et al. |
| 2008/0027273 A1 | 1/2008 | Gutternman |
| 2008/0027480 A1 | 1/2008 | Van Der Burg et al. |
| 2008/0027560 A1 | 1/2008 | Jackson et al. |
| 2008/0035160 A1 | 2/2008 | Woodson et al. |
| 2008/0053461 A1* | 3/2008 | Hirotsuka .......... A61B 17/0642 128/848 |
| 2008/0058584 A1 | 3/2008 | Hirotsuka et al. |
| 2008/0066766 A1* | 3/2008 | Paraschac ................ A61F 5/56 128/848 |
| 2008/0066767 A1 | 3/2008 | Paraschac et al. |
| 2008/0066769 A1 | 3/2008 | Dineen et al. |
| 2008/0077162 A1 | 3/2008 | Domingo |
| 2008/0082113 A1 | 4/2008 | Bishop et al. |
| 2008/0091219 A1 | 4/2008 | Marshall et al. |
| 2008/0103506 A1 | 5/2008 | Volpi et al. |
| 2008/0154286 A1 | 6/2008 | Abbott et al. |
| 2008/0208265 A1 | 8/2008 | Frazier et al. |
| 2008/0275469 A1 | 11/2008 | Fanton et al. |
| 2009/0014012 A1 | 1/2009 | Sanders |
| 2009/0018554 A1 | 1/2009 | Thorne et al. |
| 2009/0026236 A1* | 1/2009 | Krause .................. A45C 13/30 224/264 |
| 2009/0069824 A1 | 3/2009 | Chu |
| 2009/0099598 A1 | 4/2009 | McDevitt et al. |
| 2009/0105751 A1* | 4/2009 | Zentgraf ............ A61B 17/0482 606/206 |
| 2009/0105753 A1 | 4/2009 | Greenhalgh et al. |
| 2009/0125043 A1 | 5/2009 | Dehnad |
| 2009/0210005 A1 | 8/2009 | Dinger |
| 2009/0228041 A1 | 9/2009 | Domingo |
| 2009/0248071 A1 | 10/2009 | Saint et al. |
| 2009/0318938 A1 | 12/2009 | Hathaway et al. |
| 2009/0318958 A1 | 12/2009 | Ochiai |
| 2009/0319046 A1 | 12/2009 | Krespi |
| 2010/0004683 A1 | 1/2010 | Hoof et al. |
| 2010/0106169 A1 | 4/2010 | Niese et al. |
| 2010/0114123 A1 | 5/2010 | Nason |
| 2010/0132719 A1 | 6/2010 | Jacobs et al. |
| 2010/0160962 A1 | 6/2010 | Dreyfuss et al. |
| 2010/0198235 A1 | 8/2010 | Pierce et al. |
| 2010/0262184 A1 | 10/2010 | Dreyfuss |
| 2011/0004242 A1 | 1/2011 | Stchur |
| 2011/0155142 A1* | 6/2011 | Boucher .................. A61F 5/56 128/848 |
| 2011/0230974 A1* | 9/2011 | Musani ............. A61B 17/0401 623/23.7 |
| 2011/0245850 A1* | 10/2011 | van der Burg ......... A61B 90/39 606/145 |
| 2011/0308529 A1 | 12/2011 | Gillis et al. |
| 2012/0017919 A1 | 1/2012 | Gillis et al. |
| 2012/0132214 A1 | 5/2012 | Gillis et al. |
| 2012/0277767 A1 | 11/2012 | Powers et al. |
| 2013/0233324 A1 | 9/2013 | Witt et al. |
| 2013/0345724 A1 | 12/2013 | van der Burg et al. |
| 2014/0074158 A1 | 3/2014 | Feezor et al. |
| 2015/0250476 A1 | 9/2015 | Feezor et al. |
| 2017/0000477 A1 | 1/2017 | van der Burg et al. |
| 2017/0020506 A1 | 1/2017 | Feezor et al. |
| 2019/0167264 A1 | 6/2019 | Feezor et al. |
| 2019/0175169 A1 | 6/2019 | van der Burg et al. |
| 2020/0078194 A1 | 3/2020 | Feezor et al. |

FOREIGN PATENT DOCUMENTS

| | | |
|---|---|---|
| WO | WO 2002/039905 | 5/2002 |
| WO | WO 2007/073931 | 7/2007 |
| WO | WO 2011/123714 | 10/2011 |
| WO | WO 2011/151745 | 12/2011 |
| WO | WO 2014/039848 | 3/2014 |
| WO | WO 2015/134763 | 9/2015 |

OTHER PUBLICATIONS

Abraham Lapidot, M.D. and Nahum Ben-Hur, M.D., Fastening the Base of the Tongue Forward to the Hyoid for Relief of Respiratory Distress in Pierre Robin Syndrome, 56 Plastic & Reconstructive Surgery 89 in 4 pages (1975).

Beverly Douglas, M.D., The Treatment of Micrognathia Associated with Obstruction by a Plastic Procedure, in 1 Plastic & Reconstructive Surgery 300, in 12 pages (Warren B. Davis ed., The Williams & Wilkins Co. 1946).

Chris T. Oeconomopoulos, M.D., The Value of Glossopexy in Pierre-Robin Syndrome, 262 NEJM 1267 in 3 pages (1960).

Frank G. DeLuca, M.D., and Conrad W. Wesselhoeft, M.D., Surgically Treatable Causes of Neonatal Respiratory Distress, 5 Clinics in Perinatology 377 in 19 pages (1978).

H. Faye-Lund, G. Djupesland, & T. Lyberg, Glossopexia—Evaluation of a New Surgical Method for Treating Obstructive Sleep Apnea Syndrome, 492 Acta Oto-Laryngologica 46 in 4 pages (1990).

M.R. Wexler, H. Kaplan, K. Abu-Dalu, & M. Rousso, A Dynamic Fixation of the Base of the Tongue to the Mandible Using De-epithelized Tongue Flap in the Pierre Robin Syndrome, 4 Chirurgia Plastica 297 in 5 pages (1979).

Peter Randall, M.D., The Robin Anomalad: Micrognathia and Glossoptosis with Airway Obstruction, Reconstructive Plastic Surgery 2241 in 13 pages (2d ed., W.B. Saunders Co. 1977).

Robert M. Woolf, M.D., Nicholas Georgiade, M.D., and Kenneth L. Pickrell, M.D., Micrognathia and Associated Cleft Palate, 26 Plastic & Reconstructive Surgery 199 in 4 pages (1960).

Robert W. Riley, DDS, MD, Nelson B. Powell, MD and Christian Guilleminault, MD, Obstructive Sleep Apnea and the Hyoid: A Revised Surgical Procedure, 111 Otolaryngol Head Neck Surgery 717 in 5 pages (1994).

Stephen R. Lewis, M.D., John B. Lynch, M.D., & Truman G. Blocker, Jr., M.D., Fascial Slings for Tongue Stabilization in the Pierre Robin Syndrome, 42 Plastic & Reconstructive Surgery 237 in 6 pages (1968).

Search Report dated Apr. 28, 2015 in EP Patent Application No. 117634 77.4 in 2 pages.

International Search Report dated Jun. 10, 2011 in International Patent Application No. PCT/US2011/030829 in 16 pages.

International Search Report dated Dec. 12, 2013 in International Patent Application No. PCT/US2013/058547 in 7 pages.

International Search Report/Written Opinion for application No. PCT/US2015/018944 dated Jun. 10, 2015 in 10 pages.

* cited by examiner

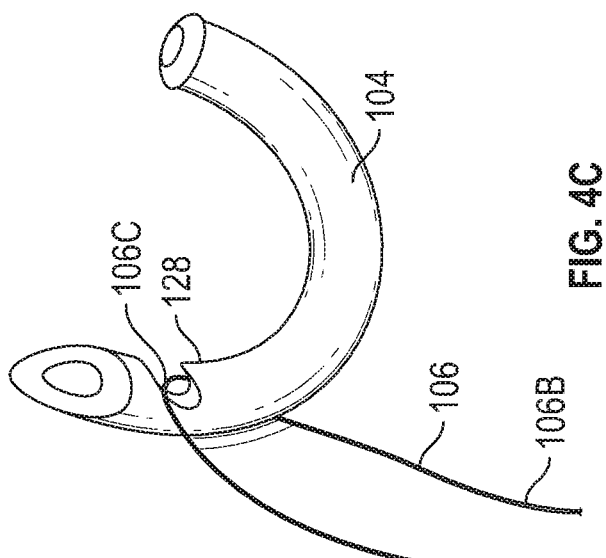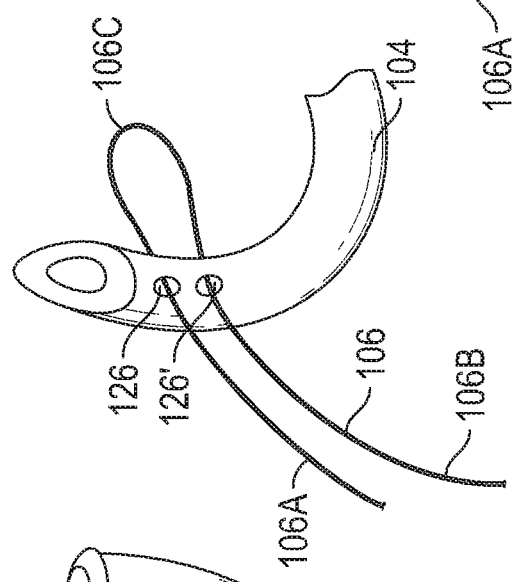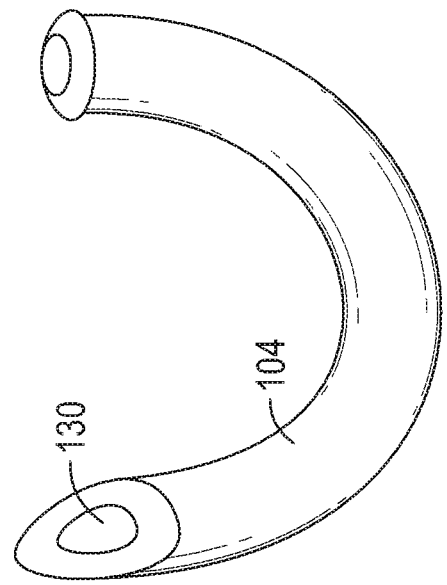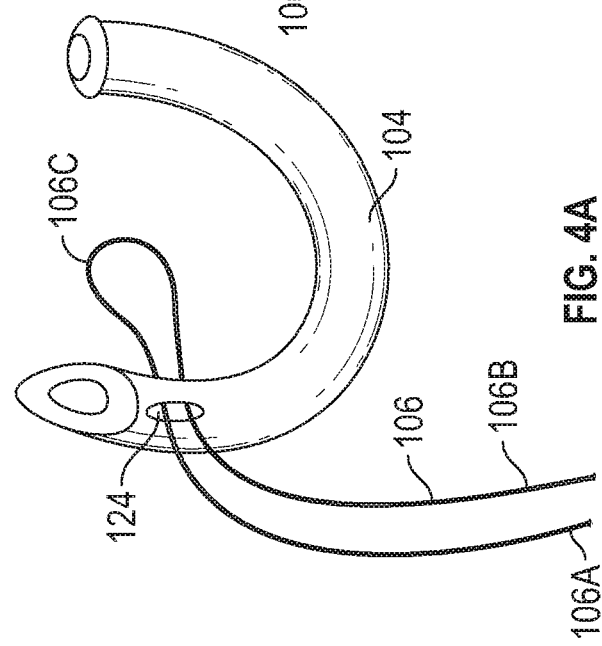

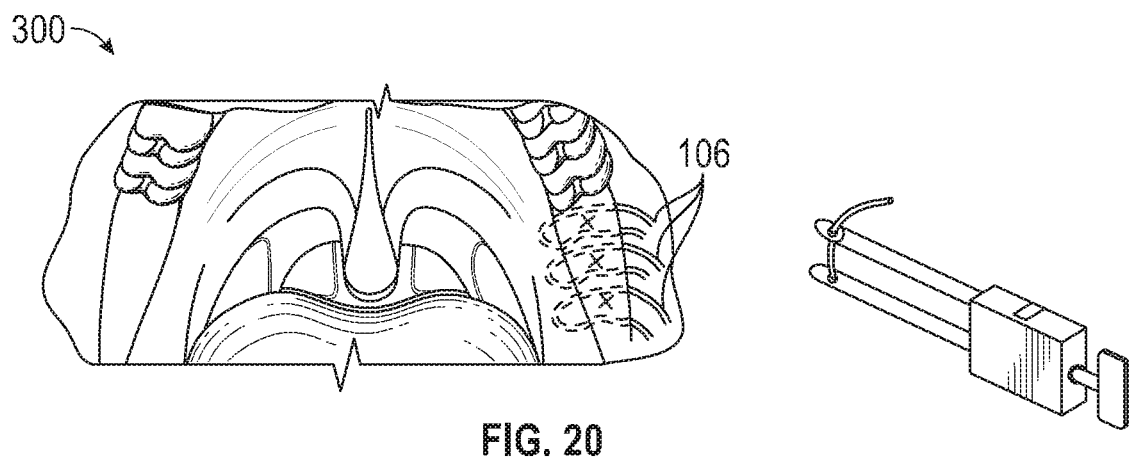
FIG. 20
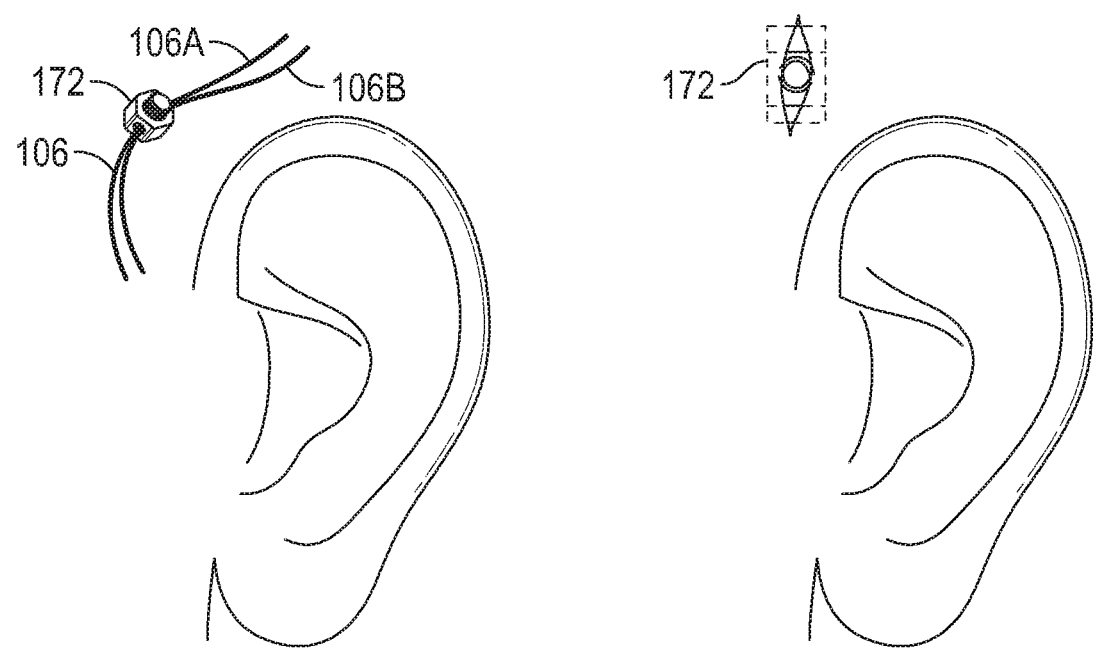
FIG. 21A
FIG. 21B

SUTURE PASSER SYSTEMS AND METHODS FOR TONGUE OR OTHER TISSUE SUSPENSION AND COMPRESSION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation application of U.S. application Ser. No. 14/639,774 filed Mar. 5, 2015, which claims the priority benefit under 35 U.S.C. § 119(e) as a nonprovisional application of U.S. Provisional Application No. 61/948,473, filed on Mar. 5, 2014, which are hereby incorporated by reference in its entirety Also incorporated by reference in their entireties is U.S. Pat. No. 8,460,322 issued on Jun. 11, 2013, and U.S. Pat. Pub. No. 2014/0074518 A1 published on Mar. 13, 2014.

BACKGROUND

Field

In some aspects, the invention relates generally to suture passer systems and methods for tissue suspension and tissue compression. Disclosed herein are systems and methods for tissue suspension using one or more sutures, implants, fasteners and/or bone anchors for treating obstructive sleep apnea.

Description of the Related Art

In many surgical procedures, there is a need to pass a suture deep into tissue. Sometimes, a surgeon needs to pass a suture deep into tissue to suspend the tissue by fixing the suture to bone. In particular, one such surgical procedure is suspension of tissues for treating conditions such as obstructive sleep apnea (OSA).

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velo-pharyngeal insufficiency where food and liquids enter into the nasopharynx during swallowing.

Laser-assisted uvulopalatopharyngoplasty (LAUP) is a similar procedure to UPPP that uses a $CO_2$ laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Another surgical procedure performed to treat OSA is suture based tongue suspension. However, current techniques for suture based tongue suspension require the passage of suture through the tongue and into the oral space. This technique carries with it significant risks of infection as well as difficulty in accessing the optimal placement for the suspension suture.

Notwithstanding the foregoing, there remains a need for improved methods and devices for treating various conditions, including but not limited to obstructive sleep apnea. There is also a need for improved devices and methods for delivering suture into tissue. Specifically with respect to current methods for tissue suspension and compression, there is a need to reduce infection risk due to suture exposure to the oral cavity, to improve the surgeon's range and ability to precisely locate and orient the suture, and to improve the ability of surgeons to properly tension the suture by eliminating the need to perform knot-tying while simultaneously controlling the final tension of the suture.

SUMMARY

The present disclosure provides suture passer system and methods for tissue suspension or compression.

In some embodiments, a suture passer is provided. The suture passer can comprise a proximal handle. The suture passer can comprise an elongate shaft having a proximal end, a distal end, and a longitudinal axis. The suture passer can comprise a suture passing element coupled to the distal end of the shaft. In some embodiments, the suture passing element is movable with respect to the shaft, and configured to swivel with respect to the shaft in an arc of at least about 90 degrees. In some embodiments, the suture passing element comprises a feature to engage the suture. In some embodiments, the suture passing element comprises a tube.

In some embodiments, a suture passer is provided. The suture passer can comprise an elongate shaft. The suture passer can comprise a suture passing element coupled to the elongate shaft. In some embodiments, the suture passing element is configured to swivel with respect to the elongate shaft. The suture passer can comprise a second stage element carried within the suture passing element. In some embodiments, the second stage element can be configured to extend from and retract into the suture passing element. In some embodiments, the second stage element can be configured to exit an opening at or near a distal end of the suture passing element and form a path through tissue. The suture passer can comprise a suture carried by the second stage element. In some embodiments, the second stage element comprises a grasping element operably connected to the suture. In some embodiments, the grasping element comprises a snare. In some embodiments, the grasping element comprises movable jaws.

In some embodiments, a suspension line is provided. The suspension line can comprise a suture. The suspension line can comprise an overmolded segment. The suspension line can comprise a feature between the suture and the overmolded segment which serves as a bearing.

In some embodiments, a method is provided. The method can include the step of providing an implant having a first end and a second end. The method can include the step of securing the first end of the implant to the palatopharyngeal arch. The method can include the step of tensioning the implant. The method can include the step of securing the second end of the implant to a tissue selected from the group consisting of: the superior pharyngeal constrictor muscle, palatopharyngeal arch, and palatoglossal arch.

In some embodiments, the implant comprises barbs. In some embodiments, the implant comprises suture loops. The method can include the step of securing the implant to a bone anchor. The method can include the step of adjusting the tension of the implant post-operatively.

In some embodiments, a method is provided. The method can include the step of moving a portion of a tissue selected from the group consisting of: the superior pharyngeal constrictor muscle, palatopharyngeal arch, and palatoglossal arch. The method can include the step of securing a fastener to a tissue selected from the group consisting of: the superior pharyngeal constrictor muscle, palatopharyngeal arch, and palatoglossal arch.

In some embodiments, a method is provided. The method can include the step of forming a loop around the hyoid bone. The method can include the step of securing the loop to a bone anchor, wherein the bone anchor is located on the mandible. In some embodiments, the loop is a girth hitch. In some embodiments, the loop is formed by an implant comprising a longitudinally extending tail and an implant head. In some embodiments, the implant comprises a ratchet for tensioning the loop.

In some embodiments, a method is provided. The method can include the step of forming a hole in the hyoid bone. The method can include the step of passing an implant through the hole in a collapsed configuration. The method can include the step of expanding the implant to an expanded configuration, wherein the implant is unable to pass through the hole in the expanded configuration. In some embodiments, the implant comprises expandable barbs.

In some embodiments, a suspension line for tensioning tissue is provided. The suspension line can comprise a suture having a first thickness dimension. The suspension line can comprise an elastomer surrounding a portion of the suture having a second thickness dimension greater than the first thickness dimension. The suspension line can comprise at least one bearing element configured to allow the suture to move with respect to the elastomer while maintaining the flexibility of the suture.

In some embodiments, the at least one bearing element is at least partially covered by the elastomer. In some embodiments, the at least one bearing element comprises a knot. In some embodiments, the at least one bearing element comprises a bead. In some embodiments, the at least one bearing element comprises a coil. In some embodiments, the coil comprises polypropylene. In some embodiments, the elastomer comprises silicone. In some embodiments, the elastomer is at least partially radiopaque. In some embodiments, the elastomer is compounded with a radiopacifier.

In some embodiments, a suture passer is provided. The suture passer can comprise a first section with a first distal tip and a first proximal handle. The suture passer can comprise a second section with a second distal tip and a second proximal handle. The suture passer can comprise a slot on the sidewall of the first section. The suture passer can comprise a first interior lumen extending through a portion of the first section and in communication with the slot. The suture passer can comprise a plunger configured to enter the slot and the first interior lumen and move a suture toward the second section.

In some embodiments, the plunger comprises a feature to engage the suture. The suture passer can comprise a second interior lumen extending through a portion of the second section. In some embodiments, the plunger is configured to enter the second interior lumen. In some embodiments, the second section comprises a snare. In some embodiments, the first section is configured to pivot relative to the second section. In some embodiments, the plunger comprises a head, wherein the head has at least one dimension larger than a corresponding dimension of the plunger. In some embodiments, the first distal tip is curved. In some embodiments, the second distal tip is curved. In some embodiments, the first interior lumen is open at the first distal tip. In some embodiments, the second interior lumen is open at the second distal tip.

In some embodiments, a method of using a suture passer is provided. The method can include the step of providing a suture passer comprising a first section with a first distal tip, a second section with a first distal tip, and a first interior lumen extending through a portion of the first section. The method can include the step of advancing the suture passer around a hyoid bone. The method can include the step of passing a plunger into the first interior lumen.

The method can include the step of engaging the plunger with a suture. The method can include the step of engaging the suture with a snare. The method can include the step of engaging the suture with a feature of the second section. The method can include the step of disengaging the suture as the plunger is retracted through the first interior lumen. The method can include the step of protruding the plunger from the first interior lumen toward the second distal tip. In some embodiments, the suture passer comprises a second interior lumen extending through a portion of the second section, further comprising passing the plunger into the second interior lumen. The method can include the step of engaging the suture with a snare coupled to the second section. The method can include the step of engaging the suture with a feature coupled to the second section. The method can include the step of engaging a suture with the second section. The method can include the step of advancing the plunger toward the suture. The method can include the step of engaging the suture with the plunger. The method can include the step of moving the suture through the first interior lumen as the plunger is retracted. The method can include the step of moving the suture through the first interior lumen as the first section is pivoted.

In some embodiments, a method is provided. The method can include the step of providing a suture having a first strand, a second strand, and an arc between the first strand and the second strand. The method can include the step of placing the arc on one side of the hyoid bone. The method can include the step of placing the first strand and the second strand on the other side of the hyoid bone. The method can include the step of forming a girth hitch around the hyoid bone. The method can include the step of securing the first strand and the second strand to a bone anchor. In some embodiments, the bone anchor is located on the mandible. In some embodiments, the system further includes a second suture comprising a third strand, a fourth strand, and a second arc between the third strand and the fourth strand. The method can include the step of coupling the third strand to the first strand. The method can include the step of pulling the third strand to form the girth hitch. The method can include the step of placing the second arc under the first arc. The method can include the step of pulling the suture such that the second arc is on one side of the hyoid bone and both the third and fourth strands are on other side of the hyoid bone. In some embodiments, the system further comprises an elastomer surrounding a portion of the suture. In some embodiments, the system further comprises an at least one bearing element on the suture. In some embodiments, the at least one bearing element is at least partially covered by the elastomer.

In some embodiments, an apparatus is provided having a shaft for passing a suture and a needle coupled to the shaft. The needle is freely rotatable with respect to the shaft. The needle can include a feature to engage the suture. The needle can include a tube. The apparatus can have a second stage element configured to extend from the needle.

In some embodiments, an apparatus is provided having a suture, an overmolded segment, and a feature between the suture and the overmolded segment which serves as a bearing.

In some embodiments, a method is provided which comprises the steps of providing an implant having a first end and a second end, securing the first end of the implant to the palatopharyngeal arch, tensioning the implant, and securing the second end of the implant to a tissue selected from the group consisting of: the superior pharyngeal constrictor muscle, palatopharyngeal arch, and palatoglossal arch. The implant can include barbs. The implant can include suture loops. The method can include the step of securing the implant with a bone anchor. The method can include the step of adjusting the tension of the suture loops post-operatively.

In some embodiments, a method is provided which comprises the steps of moving a portion of a tissue selected from the group consisting of: the superior pharyngeal constrictor muscle, palatopharyngeal arch, and palatoglossal arch; and securing a fastener to a tissue selected from the group consisting of: the superior pharyngeal constrictor muscle, palatopharyngeal arch, and palatoglossal arch.

In some embodiments, a method is provided which comprises the steps forming a loop around the hyoid bone, and securing the loop to a bone anchor, wherein the bone anchor is located on the mandible. The loop can be a girth hitch. The loop can be formed by an implant comprising a longitudinally extending tail and an implant head. The implant can include a ratchet.

In some embodiments, a method is provided which comprises the steps of forming a hole the hyoid bone; passing an implant through the hole in a collapsed configuration; and expanding the implant to an expanded configuration, wherein the implant is unable to pass through the hole. The implant can include expandable barbs.

Also disclosed herein is a suture passer comprising one or more of: a proximal handle; an elongate shaft having a proximal end, a distal end, a tubular body, and a longitudinal axis; a needle coupled to the distal end of the shaft, the needle having an arcuate deployed configuration, wherein the needle is movable with respect to the shaft, and configured to swivel with respect to the shaft in an arc of at least about 90 degrees; and a control on the proximal handle configured to swivel the needle with respect to the shaft. The needle can comprise a feature to engage the suture, and comprise a tube in some embodiments.

In some embodiments, disclosed herein is a suture passer comprising one or more of: a proximal handle having a first actuator control and a second actuator control; a first elongate shaft extending distally from the handle; a first needle carried within the first elongate shaft, the first needle configured to extend from and retract into the first elongate shaft, the first needle having a straight configuration when located within the first elongate shaft, the first needle configured to exit an opening at or near a distal end of the first elongate shaft and form a curved or lateral path through tissue upon actuation of the first actuator control; and a second needle carried within the first needle, the second needle configured to extend from and retract into the first needle, the second needle having a straight configuration when located within the first elongate shaft, the first needle configured to exit an opening at or near a distal end of the first needle and form a curved or lateral path through tissue upon actuation of the second actuator control, the second needle having an extended geometry that is different from that of the first needle; and a suture carried by the second needle. The second needle can comprise a grasping element operably connected to the second needle, such as, for example, a snare or movable jaws.

Also disclosed herein is a suspension line comprising a suture; an overmolded segment; and a feature between the suture and the overmolded segment which serves as a bearing.

In another embodiment, disclosed is a method comprising providing an implant having a first end and a second end; securing the first end of the implant to the palatopharyngeal arch; tensioning the implant; and securing the second end of the implant to a tissue selected from the group consisting of: the superior pharyngeal constrictor muscle, palatopharyngeal arch, and palatoglossal arch. The implant can comprises barbs and/or suture loops. The implant can also be secured with a bone anchor. The tension of the suture loops can be adjusted during the procedure, or post-operatively, such as 1 hour, 6 hours, 1 day, 1 week, 1 month, or more post-operatively.

Also disclosed is a method comprising moving a portion of a tissue selected from the group consisting of: the superior pharyngeal constrictor muscle, palatopharyngeal arch, and palatoglossal arch; and securing a fastener to a tissue selected from the group consisting of: the superior pharyngeal constrictor muscle, palatopharyngeal arch, and palatoglossal arch.

Also disclosed is a method comprising: forming a loop around the hyoid bone; and securing the loop to a bone anchor, wherein the bone anchor is located on the mandible. The loop can be a girth hitch. The loop can be formed by an implant comprising a longitudinally extending tail and an implant head. The implant can also comprise a ratchet for tensioning the loop.

In some embodiments, disclosed is a method comprising: forming a hole in the hyoid bone; passing an implant through the hole in a collapsed configuration; and expanding the implant to an expanded configuration, wherein the implant is unable to pass through the hole. The implant can comprise expandable barbs.

Further disclosed herein is a suspension line for tensioning tissue, comprising: a suture having a first thickness dimension; a elastomer surrounding a portion of the suture and defining a central segment of the suspension line having a second thickness dimension greater than the first thickness dimension; and at least one bearing element on the central segment of the suspension line, the bearing element configured to provide a rigid bearing to allow the suture to move with respect to the elastomer (e.g., silicone) while maintaining the flexibility of the suture. The at least one bearing element can be at least partially covered by the elastomer. The bearing element can include, for example, a knot, a bead, and/or a coil. The coil can comprise polypropylene, for example. The elastomer can be at least partially radiopaque, and/or compounded with a radiopacifier, such as barium sulfate for example.

BRIEF DESCRIPTION OF THE DRAWINGS

FIGS. 4A-4D illustrate embodiments of a suture passing element.

FIG. 20 illustrates an embodiment of a method of inserting a suture.

FIGS. 21A-21B illustrate an embodiment of a method of using a bone anchor.

DETAILED DESCRIPTION

In some embodiment, disclosed is a suture passer system and method for passing a suture (e.g., a suspension line, a tether, a tether loop, a suture, a suture loop, suture tape, an implant, etc.) through tissue to suspend or compress the tissue. The term "suture" as used herein, unless otherwise specified or limited, is intended to have its ordinary meaning and is also intended to include all structures, including any of the aforementioned or later-described examples, that can be passed through tissue using the devices described herein.

Figure 1A:
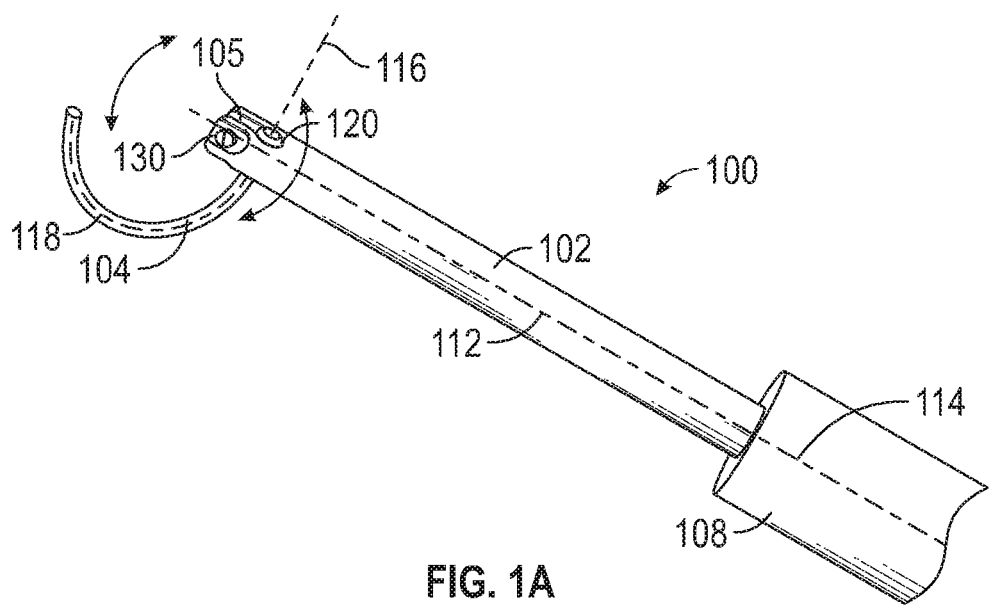
FIGS. 1A-1C illustrate an embodiment of a suture passer with a suture passing element.

As illustrated in FIG. 1A, the suture passer 100 can include a first elongate tubular body or shaft 102. The shaft 102 can releasably couple to a suture passing element 104. The suture passing element 104 can be a flexible needle. The suture passing element 104 can pass one, two, or more sutures therethrough. Portions of the one or more sutures can reside outside of the first shaft 102. The distal end of the suture passing element 104 can be sharpened to facilitate tissue penetration. In other embodiments, the distal end of the suture passing element 104 can be blunt to prevent distal penetration through the mucosa, thus preventing a through-and-through puncture. The shaft 102 can have a length of between about 4 cm to about 30 cm in some embodiments.

The suture passer 100 can include a second elongate tubular body or shaft (not shown). The second shaft can couple to a suture receiving element (not shown). The suture receiving element can be a snare, for example. The second shaft and the suture passer 100 can be substantially similar to suture passer system described in commonly owned U.S. Pat. No. 8,460,322, the entire disclosure of which is incorporated by reference. The suture passer 100 can include any feature described in in commonly owned U.S. Pat. No. 8,460,322.

The shaft 102 can extend distally from a proximal handle 108. As illustrated in FIG. 1A, the proximal end of the shaft 102 can be coupled to the handle 108. In some embodiments, the shaft 102 rotates when the handle 108 rotates. The shaft 102 can rotate about the longitudinal axis 114 of the proximal handle 108. In some embodiments, the shaft 102 can rotate independently from the handle 108. The shaft 102 can rotate about the longitudinal axis 112 of the shaft 102.

As illustrated in FIG. 1A, the suture passing element 104 can be coupled to the distal end of the shaft 102. The suture passing element 104 can rotate relative to the distal end of the shaft 102. The shaft 102 can include one, two, or more slots or apertures 105 on the sidewall of the distal end of the shaft 102. The suture passing element 104 can be located within the slot 105. In some embodiments, the suture passing element 104 is formed as an independent component from the shaft 102. The suture passing element 104 can rotate relative to the slot 105 (e.g., 0°, 10°, 20°, 30°, 40°, 50°, 60°, 70°, 80°, 90°, 100°, 110°, 120°, 130°, 150°, 160°, 170°, 180°, 190°, 200°, 210°, 220°, 230°, 240°, 250°, 260°, 270°, 280°, 290°, 300°, 310°, 320°, 330°, 340°, 350°, 360°, at least 90°, at least 180°, at least 270°, etc., or a range including any two of the foregoing values, such as between about 0° and about 180° for example).

The suture passing element 104 can function as a hook. The suture passing element 104 can be moved in position relative to the shaft 102. The shaft 102 can be rotated relative to the suture passing element 104 after the suture passing element 104 hooks, or passes an elongate element around a bone. The suture passing element 104 can rotate when the shaft 102 is held stationary. The shaft 102 can rotate when the suture passing element 104 is held stationary. The suture passing element 104 and the shaft 102 can rotate at the same time, in the same directions and/or orientations or a different directions and/or orientations. The suture passing element 104 can rotate relative to the longitudinal axis 112 of the shaft 102. The suture passing element 104 can rotate relative to the longitudinal axis 114 of the proximal handle 108. The suture passing element 104 can rotate about an axis 116, wherein axis 116 is perpendicular to the longitudinal axis 112 of the shaft 102. The suture passing element 104 can rotate about one, two, or more axes. In some embodiments, the suture passing element 104 while rotating in an arc, offset from the longitudinal axis of the shaft 102, during at least one point during rotation the path of the arc intersects the longitudinal axis 112 of the shaft 102. The degree of rotation of the suture passing element 104 can be, in some embodiments, at least about 45°, 90°, 135°, 180°, 225° or more, or between about 90° and 180°, 135-225°, or different ranges including two of the foregoing values thereof for example.

Figure 1B:
Figure 1C:
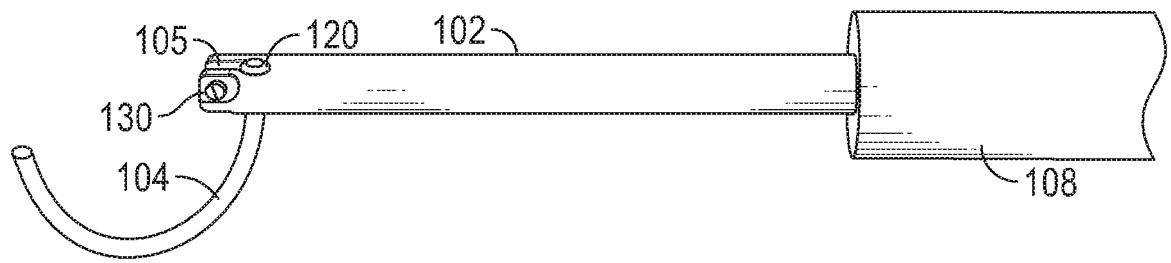
Figure 2A:
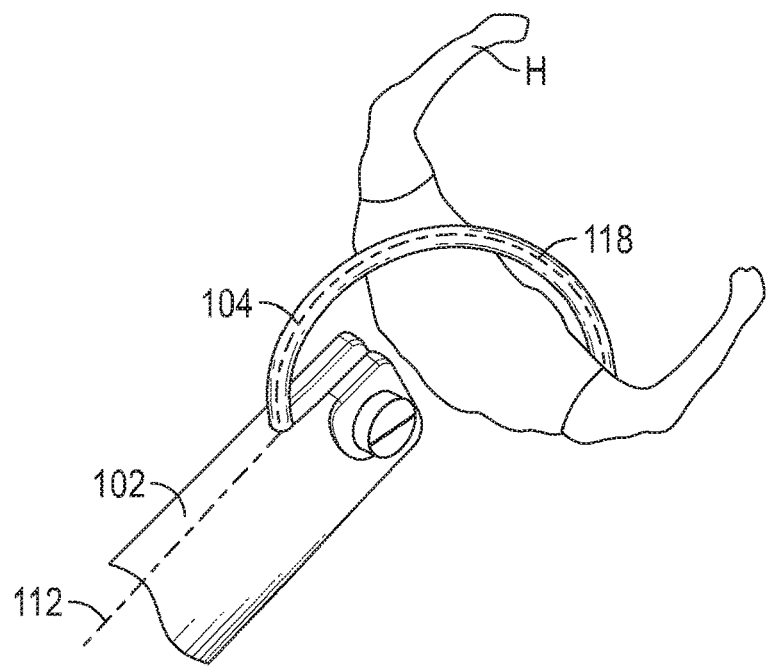
FIGS. 2A-2C illustrate a method of using the suture passer of FIG. 1A.

The suture passing element 104 can include a longitudinal axis 118. In some orientations, the longitudinal axis 118 of the suture passing element 104 is aligned with the longitudinal axis 112 of the shaft 102, as shown in FIGS. 1A and 2A. In some orientations, the longitudinal axis 118 of the suture passing element 104 is not aligned with the longitudinal axis 112 of the shaft 102, as shown in FIGS. 1B, 1C, and 2C as well as the schematic of FIG. 1C clarifying certain features. The suture passing element 104 can be rotated relative to the slot 105 as shown in FIG. 1C.

In some embodiments, a mechanism (not shown) can control the rotation of the suture passing element 104 relative to the shaft 102. The mechanism 110 can be housed within the shaft 102. The suture passing element 104 can be coupled to the shaft 102. The suture passing element 104 can be retained in the slot 105. The slot 105 can include a bushing 120 or other device known in the art to permit free rotation. The distal end of the shaft 102 can be split to house the bushing 120. A component 130 such as a fastener can couple the split distal end of the shaft 102 to prevent the disengagement and/or loosening of the bushing 120. In some embodiments, the bushing 120 provides friction to hold the suture passing element 104 relative to the shaft 102. The torque exerted by rotating the shaft 102 can rotate the shaft 102 relative to the suture passing element 104.

Figure 2B:
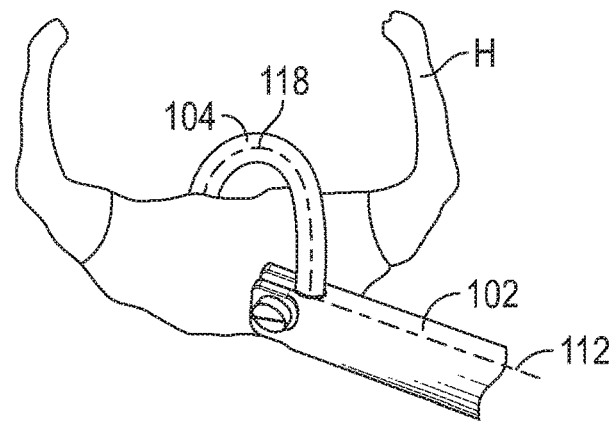
Figure 2C:
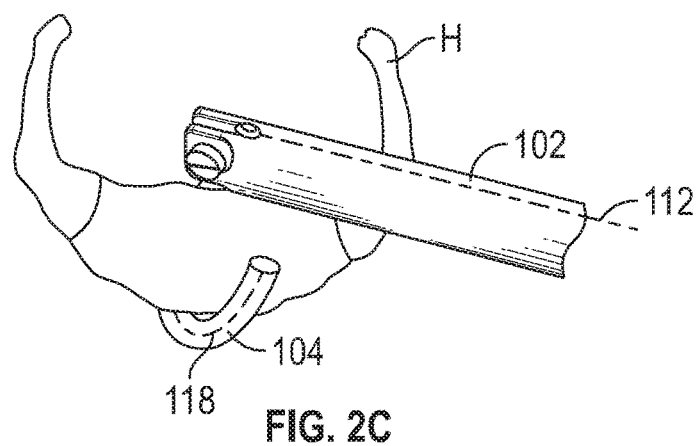
Figure 3A:
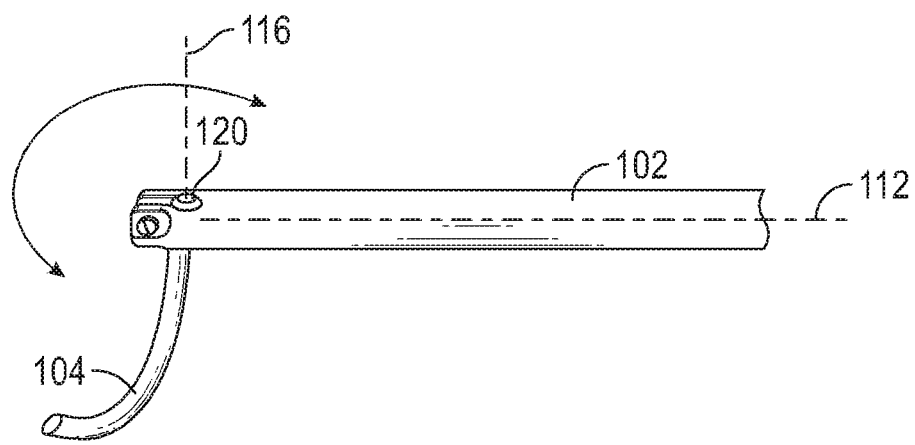
FIGS. 3A-3D illustrate an embodiment of a suture passer with a suture passing element.
Figure 3B:
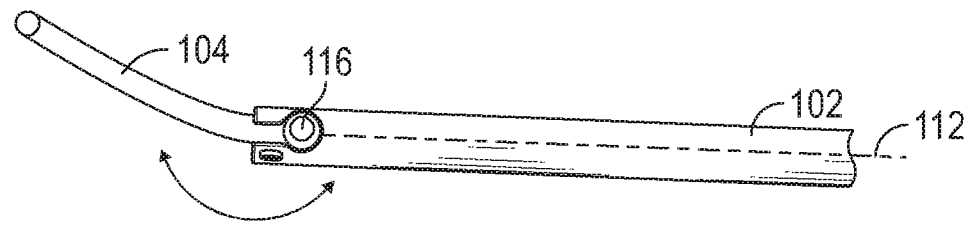
Figure 3C:
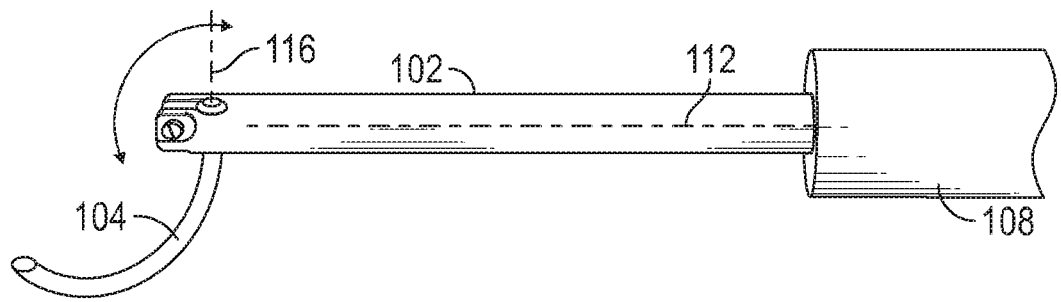
Figure 3D:
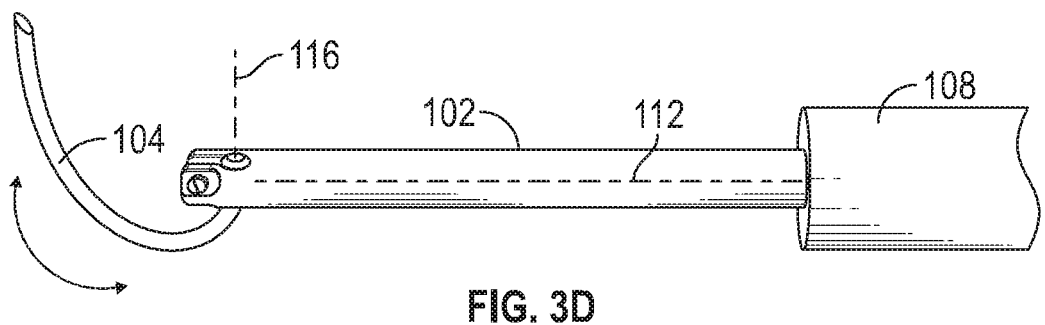

As illustrated in FIGS. 2A-2C, a method of using the suture passer 100 is shown with respect to the hyoid bone. The method illustrates a generally superior to inferior approach. The longitudinal axis 118 of the suture passing element 104 can be generally aligned with the longitudinal axis 112 of the shaft 102. The suture passing element 104 can extend from the distal end of the shaft 102. The shaft 102 can be manipulated relative to the hyoid bone until the suture passing element 104 surrounds, such as least partially circumscribes a portion of the hyoid bone. FIG. 2B illustrates the front view of the approach. As shown in FIGS. 2A-2B, the longitudinal axis 118 of the suture passing element 104 is aligned with the longitudinal axis 112 of the shaft 102. The suture passing element 104 can hook or otherwise pass an elongate element such as a suture around the hyoid bone. The shaft 102 can be rotated relative to the suture passing element 104 and/or the suture passing element 104 can be rotated relative to the shaft. FIG. 2C illustrates the suture passing element 104 in a position after a completed pass in some embodiments. The shaft 102 is rotated relative to the suture passing element 104 a different position relative to the hyoid bone. The longitudinal axis 118 of the suture passing element 104 is not aligned with the longitudinal axis 112 of the shaft 102.

As illustrated in FIGS. 3A-3D, the suture passing element 104 can rotate relative to the shaft 102. This can be completed by an internal mechanism to actively rotate the suture passing element 104, overcoming frictional forces between the shaft 102 and the suture passing element 104. The suture passing element 104 can be coupled to the shaft 102 via the bushing 120. The suture passing element 104 can rotate in an arc about, or at least about 15 degrees, 30 degrees, 60 degrees, 90 degrees, 105 degrees, 120 degrees, 135 degrees, 150 degrees, 165 degrees, 180 degrees, 195 degrees, 210 degrees, 225 degrees or more relative to the axis 116. The axis 116 can be transverse to the longitudinal axis 112 of the shaft 102.

The suture 106 can be carried by the suture passing element 104 and thereby passed around the hyoid bone. As illustrated in FIG. 4A, the suture 106 can form a suture loop including a first strand 106A, a second strand 106B and an arc (e.g., loop portion) 106C connected to and residing between the first strand 106A and the second strand 106B. The arc 106C can form a portion of a circle. The suture 106 can be pre-attached to the suture passing element 104 prior to the suture passing element 104 being passed around the hyoid bone. In other embodiments, the suture 106 can be attached to the suture passing element 104 after the suture passing element 104 is passed around the hyoid bone. The suture 106 can be passed around the hyoid bone as the suture passer 100 is retracted. The suture 106 can remain in place, around the hyoid bone, after the suture passer 100 is retracted.

As illustrated in FIGS. 4A-4D, the suture passing element 104 can have a variety of configurations. As shown in FIGS. 4A-4C, a portion of the suture passing element 104 can include one or more suture engagement mechanisms. As shown in FIG. 4A, the suture engagement mechanism can be a slot 124. The suture 106 can be inserted into the slot 124. For instance, the first strand 106A, the second strand 106, and/or the arc 106C can be inserted into the slot. The insertion of the arc 106C into the slot 124 and around the hyoid bone may facilitate the tying of a knot, as described herein. As shown, the slot 124 can be a lateral slot extending through the suture passing element 104. The suture 106 can be inserted so that the arc 106C is on one side of the suture passing element 104 and the first strand 106A and the second strand 106B of the suture 106 are on the other side of the suture passing element 104.

As shown in FIG. 4B, the suture engagement mechanism can be a plurality of holes 126, 126' (e.g., two or more holes). While two holes are shown, other configurations are contemplated (e.g., three, four, five, six, etc.). The first strand 106A of the suture 106 can be inserted into a first hole 126, and the second strand 106B of the suture 106 can be inserted into a second hole 126'. As shown, the holes 126, 126' can be laterally-facing (or alternatively distal-facing) holes with respect to the distal end of the suture passing element 104. The holes 126, 126' can extend through the suture passing element 104. The suture 106 can be inserted so that the arc 106C is on one side of the suture passing element 104 and the first strand 106A and the second strand 106B of the suture 106 are on the other side of the suture passing element 104.

As shown in FIG. 4C, the suture engagement mechanism can be a notch 128. The suture 106 can be inserted into the notch 128. As shown, the notch 128 can be a lateral notch extending along a surface of the suture passing element 104. The arc 106C of the suture 106 can be inserted into the notch 128. The first strand 106A is on one side of the suture passing element 104 and the second strand 106B is on the other side of the suture passing element 104. The slot 124, the holes 126, and the notch 128 can be formed in a distal end of the suture passing element 104. The suture 106 can be coupled to the suture passing element 104 before or after passing the suture passing element 104 is passed around a bone or tissue. In some methods, the suture engagement mechanism can guide the suture 106 around the bone or tissue.

As shown in FIG. 4D, the suture engagement mechanism can be a lumen 130. In some embodiments, the lumen 130 extends through a portion of the entire length of the suture passing element 104. The lumen 130 can include a distally-facing exit aperture, as opposed to the laterally-facing suture engagement mechanisms described with respect to FIGS. 4A-4C. The lumen 130 can extend the entire length of the suture passing element 104. The lumen 130 can extend along the length of the curved longitudinal axis 118 of the suture passing element 104. In other words, the suture passing element 104 can be in the form of a tubular structure.

Figure 5:
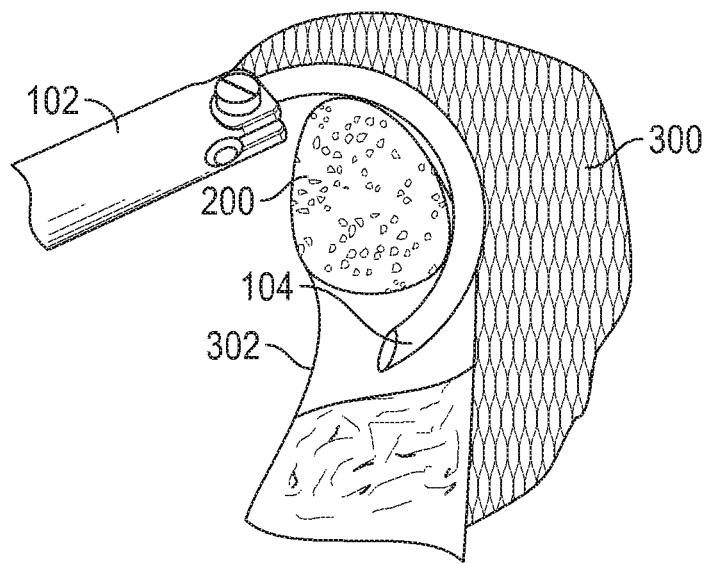
FIG. 5 illustrates the inability of a suture passer to reach a target location.
Figure 6A:
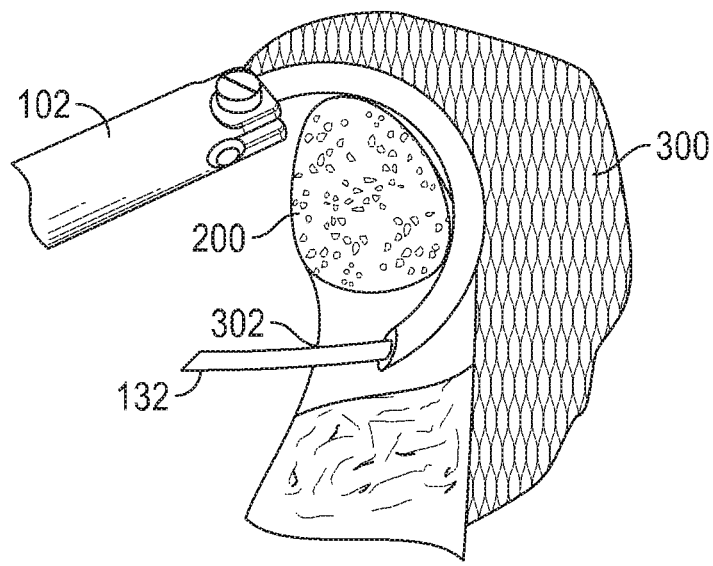
FIGS. 6A-6C illustrate an embodiment of a suture passer with a second stage element.

In some embodiments, the suture passing element 104 includes a second stage element 132 as shown in FIG. 6A. The second stage element 132 can be movable within the central lumen 130 as illustrated in FIG. 4D. The second stage element 132 can be coaxial with the suture passing element 104. The suture passing element 104 allows for the passage of the second stage element 132 through the suture passing element 104. As shown in FIG. 5, the suture passing element 104 may be unable to reach a target location 302. The suture passing element 104, in some embodiments, does not penetrate the soft tissue 300. In some cases, this limitation is caused by the interference of the shaft 102 with the soft tissue 300. In some cases, this limitation is caused by the geometry of the suture passer 100 and/or the geometry of the patient's anatomy.

This limitation has been observed, for example, in some cases when attempting to pass the suture passing element 104 close to the backside (e.g., posterior surface) of a body structure such as a bone 200, such as the hyoid bone for example. The bone 200 can be located deep within an incision. The bone 200 can be surrounded by soft tissue 300. A suture passing element 104 that is agile enough to start the pass while maintaining proximity to the bone 200 may not be sufficiently long enough to penetrate the soft tissue on the opposing side of the bone 200 to reach the target location 302. In other words, the need for agility of the suture passing element 104 may limit the length of the suture passing element 104. In other words, the design constraints of the suture passer 100 may prevent the suture passing element 104 from reaching the target location 302.

The second stage element 132 can be deployed to reach the target location 302, as shown in FIG. 6A. The second stage element 132 can be deployed through the lumen 130 of the suture passing element 104. The suture passer 100 with the second stage element 132 can penetrate the soft tissue 300 after passing around the bone 200. The suture passer 100 with the second stage element 132 can form a complete pass (e.g., a loop) around the bone 200.

Figure 6B:
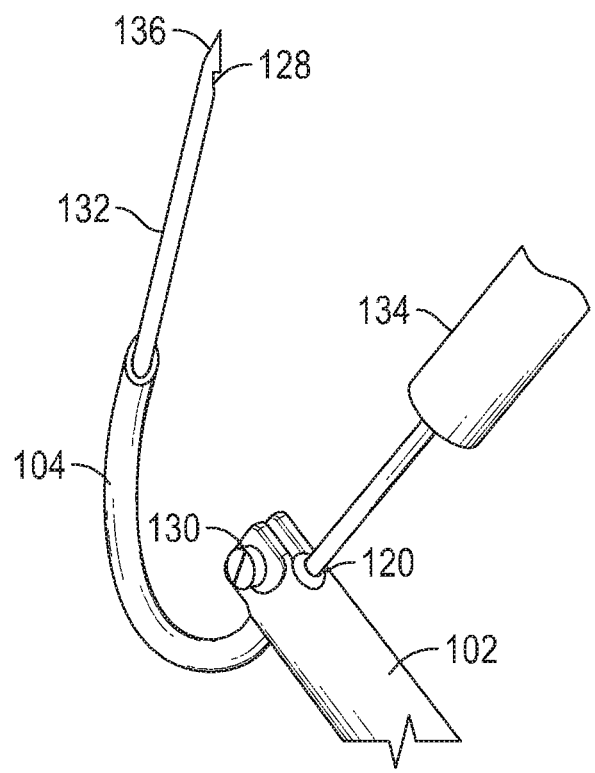
Figure 6C:
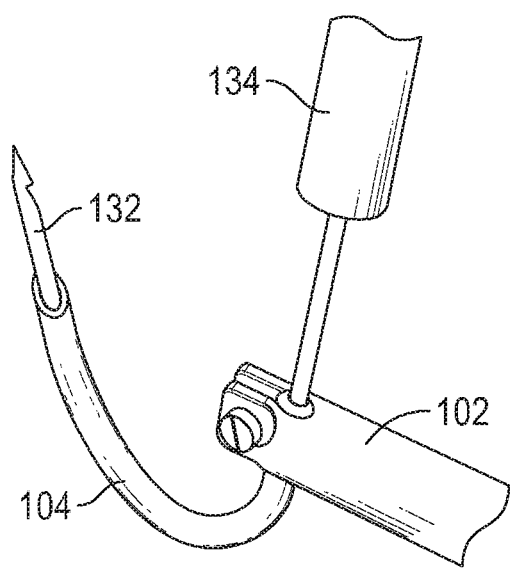

As shown in FIGS. 6A-6B, the second stage element 132 can extend distally beyond, and from a distal end of the suture passing element 104. The second stage element 132 can be a linear extension of the distal end of the suture passing element 104. As shown in FIGS. 6A-6C, a tool 134 can be used to pass the second stage element 132 through the suture passing element 104. The tool 134 can insert the second stage element 132 into the lumen 130 of the suture passing element 104. In some embodiments, the second stage element 132 can be inserted into the suture passing element 104 at the proximal end of the suture passing element 104. In some embodiments, the second stage element 132 can be inserted into the suture passing element 104 at the location where the suture passing element 104 couples with the shaft 102.

The second stage element 132 can include a needle 136, as shown in FIG. 6B. The needle 136 facilitates the additional tissue penetration to reach the target location 302. The second stage element 132 can include a suture engagement mechanism to engage suture 106. The suture engagement mechanisms can include those shown in FIGS. 4A-4D. For instance, the distal end of the second stage element 132 can include a slot, one or more holes, a notch, or a lumen or other feature.

Figure 7A:
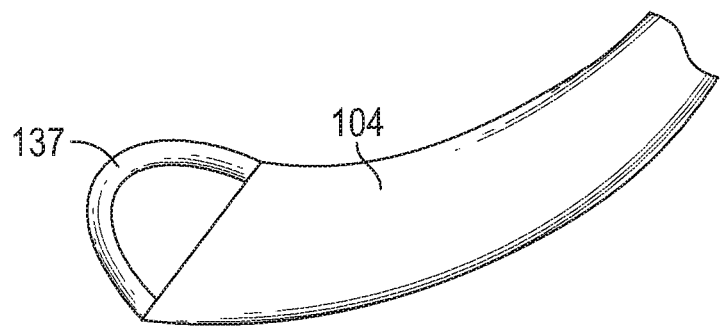
FIGS. 7A-7B illustrate an embodiment of a suture passer with a second stage element.
Figure 7B:
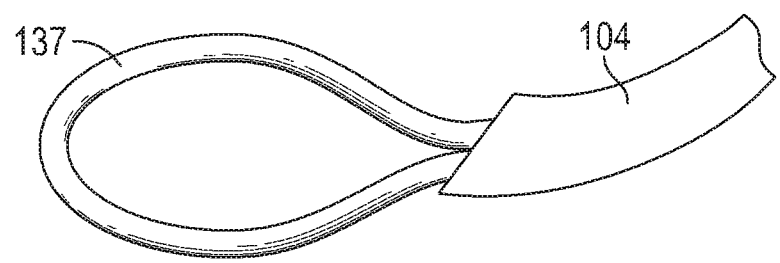

As shown in FIGS. 7A-7B, the second stage element 132 can include a snare 137. The snare 137 can extend through the lumen 130 of the suture passing element 104 as described herein. FIG. 7A shows the snare 137 retracted and FIG. 7B shows the snare 137 advanced from the distal end of the suture passing element 104. The snare 137 creates a larger target for the user to place the suture 106. In other words, the snare 137 may be, in some embodiments, easier to thread with the suture 106 than the suture engagement mechanisms such as the slot, the holes, and the notch, shown in FIGS. 4A-4D.

Figure 8A:
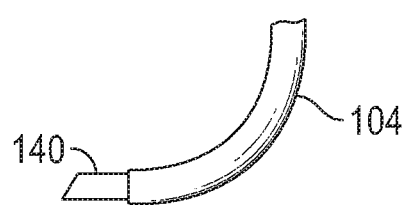
FIGS. 8A-8B illustrate an embodiment of a suture passer with a second stage element.
Figure 8B:
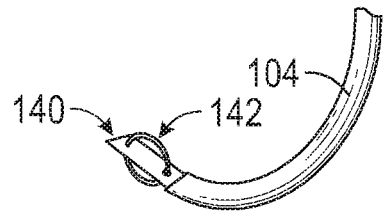

As shown in FIGS. 8A-8B, the second stage element 132 can include features of FIGS. 6A-6B and 7A-7B. The second stage element 132 can include both a needle 140 and a snare 142. The needle 140 facilitates the additional tissue penetration to reach the target location 302. The snare 142 creates a larger target for the user to place the suture 106 in the suture passer 100. The snare 142 can be operably attached to the needle 140 as illustrated, such as via laterally-facing apertures in the needle 140. FIG. 8A shows the second stage element 132 in a retracted configuration and FIG. 8B shows the second stage element 132 in an extended configuration and advanced from the distal end of the suture passing element 104.

Figure 9A:
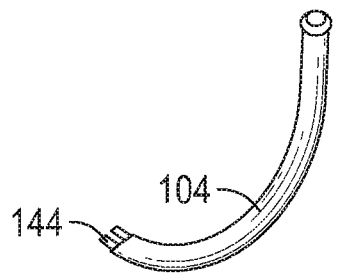
FIGS. 9A-9B illustrate an embodiment of a suture passer system with a second stage element.
Figure 9B:
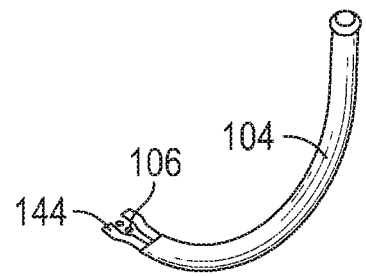

As shown in FIGS. 9A-9B, the second stage element 132 can be a grasper 144 having a plurality of movable jaws. The grasper 144 can be configured to hold one or more sutures 106 when the grasper 144 is retracted. FIG. 9A shows the grasper 144 retracted. FIG. 9B shows the grasper 144 advanced from the distal end of the suture passing element 104. In some embodiments, the grasper 144 can open when deployed from the distal end of the suture passing element 104, releasing the sutures 106. The sutures 106 can be coupled to the grasper 144 and/or the suture passer 100 prior to the suture passer 100 advancing around the bone 200. In some embodiments, the grasper 144 can close around the sutures 106 and transport the sutures 106 around the bone 200. The grasper 144 can be retracted into the suture passing element 104.

Figure 10A:
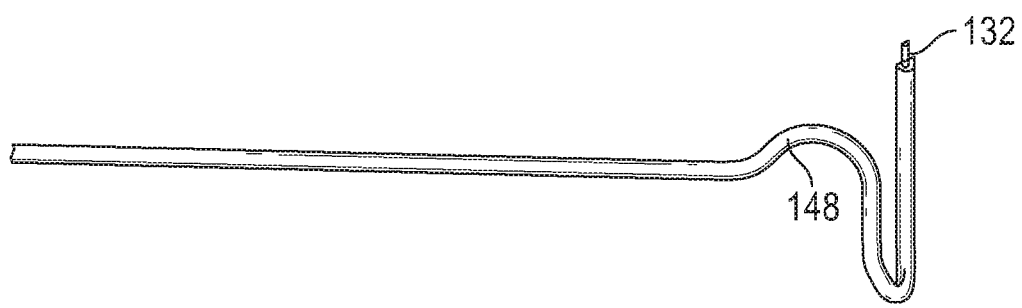
FIGS. 10A-10B illustrates an embodiment of a suture passer with a second stage element.
Figure 10B:
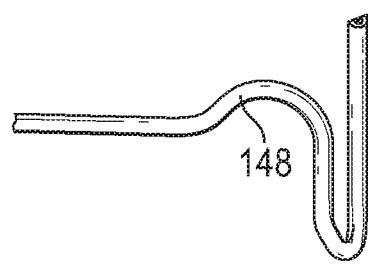

In some embodiments, the suture passing element 104 can have a complex configuration having a plurality of distal curved regions having differing radii of curvature, such as a first region having a first radii of curvature, and a second region having a second radii of curvature that is greater or less than the first radii of curvature. The first region and the second region can have convex curves, concave curves, or one convex and the other concave in some embodiments. FIGS. 10A-10B show a coiled suture passing element 148, resembling a pig's tail. The coiled suture passing element 148 can have any combination of the characteristics described herein with reference to suture passing element 104. The coiled suture passing element 148 can be tubular. The coiled suture passing element 148 can include a second stage element 132. The second stage element 132, such as a needle, facilitates the additional tissue penetration to reach the target location 302. The second stage element 132, such as a snare, can create a larger target for the user to place the suture 106. The second stage element 132, such as grasper, can hold or release sutures 106 during the pass.

In some embodiments, the outer or inner diameter of the shaft of the suture passer 100 can be between about ⅜ inch and about 1 inch. The diameter can be selected based upon the method to be performed. The outer or inner diameter of the suture passing element 104 and the coiled suture passing element 148 can be, for example, between about 1/16 inch and about ⅛ inch for methods for passing a suture around the hyoid bone.

The diameter rod or tube used to make the suture passing element 104 can depend on a number of factors. In some embodiments, it may be desirable to have the suture passing element 104 that is stiff. For instance, the suture passing element 104 may need to be stiff enough to penetrate tissue, such as tough connective tissues around the hyoid bone. The suture passing element 104 may need to be large enough to accommodate features described herein, such as suture engagement mechanisms. The suture passing element 104 may need to be large enough to accommodate additional components, such as the second stage element 132. It may be desirable to design the suture passer 100 as small as possible, for instance, with as small diameter as possible. A small diameter may minimize the amount of injury to the tissue. The diameter of second stage element 132 can be, for example between about 1/16 inch and about ⅛ inch for methods for passing a suture around the hyoid bone.

In some embodiments, the suture passing element 104 is subjected to torque. For instance, the suture passing element 104 may be subjected to torque loads when pushed through connective tissue. It can be advantageous, in some embodiments, to minimize deformations that occur when the suture passing element 104 is subjected to torque, load and/or force. The suture passing element 104 may be sufficiently stiff to navigate through connective tissue. The suture passing element 104 can be formed, in some embodiments, from a material (e.g., stainless steel) that has adequate characteristics to resist deformation during the intended use. The second stage element 132 can be formed, in some embodiments, from a material that is super-elastic (e.g., nitinol).

FIGS. 11A-11E illustrate various embodiments of sutures 106. The sutures described herein can include a variable-thickness suspension line for suspending tissue, including a suture 106 having a first thickness dimension. The suture described herein can include an elastomer surrounding a portion of the suture forming an overmolded segment 150 and defining a central segment of the suspension line having a second thickness dimension greater than the first thickness dimension. The elastomer can be overmolded onto the suture 106. The elastomer can be, for example silicone. The suture 106 can be braided. The elastomer can be overmolded over a plurality of discontinuous segments of the suture 106. The central segment of the suspension line can include one or more knots and/or one or more beads for improving adhesion between the suture and the elastomer. The suspension line could have a rounded, and/or a rectangular cross-section. As such, the sutures can either be elastic or inelastic. In some embodiments, elastic sutures can be stretched to at least about 110%, 120%, 130%, 140%, 150%, 175%, 200%, 250%, 300%, or more of their unstretched length.

The suture 106 can include at least one transition zone extending from the central segment of the suspension line to a lateral end of the suspension line, the transition zones having a thickness dimension that tapers from the second thickness dimension to the first thickness dimension. The suture 106 can have any features described in commonly owned U.S. patent application Ser. No. 14/020,617, the disclosure of which is incorporated by reference herein.

The suture 106 can be a #2 suture, or any other size depending on the desired clinical result (e.g., #1 to #6). The suture 106 can be formed from a suitable material (e.g., braided polyester, braided polyethylene). The suture 106 can include a longitudinal suture optionally coupled with additional features. The suture 106 can include two free ends. The suture 106 can include one, two, or more sections of increased thickness, that can be overmolded segments 150, or otherwise attached over the suture 106 to increase thickness of the suture. The overmolded segment 150 can be formed from, for example, silicone or other elastomer. The overmolded segment 150 can be silicone compounded with a radiopacifier, such as barium sulfate, and as such be radiopaque under an imaging modality, such as fluoroscopy or CT. In other embodiments, the suture, e.g., the overmolded segment 150, or a portion thereof is visible under other imaging modalities, such as ultrasound for example. As the suture 106 stretches under load, the overmolded segment 150 will move and stretch with the suture 106, and can advantageously provide a bearing against wear in some cases.

Figure 11A:
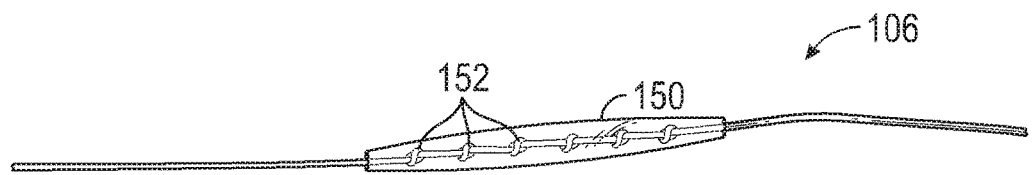
FIGS. 11A-11E illustrate embodiments of a suture.

FIG. 11A shows a suture 106 with a series of spaced-apart knots 152, or areas of increased width and/or surface area. The knots 152 can be overhand knots in some embodiments. The longitudinal suture 106 can be knotted to form an integral structure. The series of knots 152 increase adhesion between the suture 106 and the overmolded segment 150.

Figure 11B:
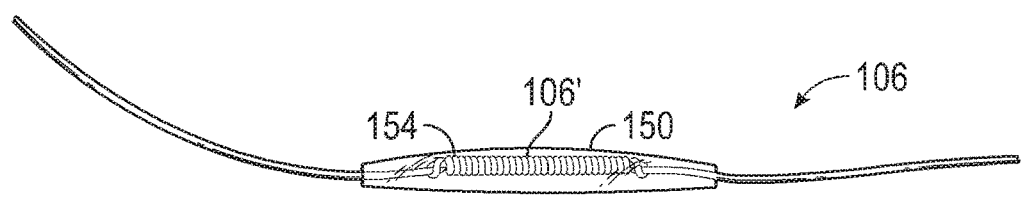

FIG. 11B shows a suture 106 with a suture braid 154. The suture braid 154 can be formed with the longitudinal first suture 106 and a second suture 106' having the same size (e.g., #2) or a different (e.g., larger or smaller) size (e.g., #5) with respect to the size of the longitudinal first suture 106. The second suture 106' is braided with the longitudinal first suture 106 and forms a suture sock as shown. The ends of the second suture 106' can be fixed to the longitudinal first suture 106 to prevent fraying. In some embodiments, heat is used to fix the second suture 106' to the longitudinal first suture 106. The suture braid 154 provides some bulk to the overmolded segment 150. The suture braid 154 can serve as a bearing.

Figure 11C:
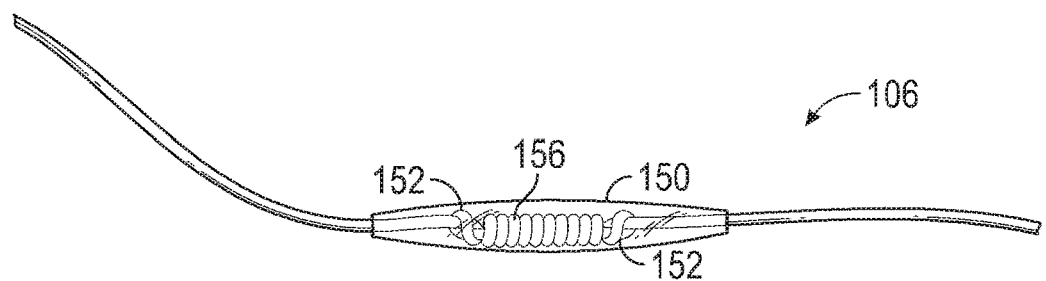

FIG. 11C shows a suture 106 with a series of beads 156. The beads 156 can be rigid or flexible beads. The beads 156 can be formed from a suitable material (e.g., glass). The beads 156 can all have the same diameter, as shown in FIG. 11C. The beads 156 can be retained on the longitudinal suture 106 by knots 152 positioned at the end of the beads 156. The knots 156 can be overhand knots. The knots 152 can be adjacent to the first and last beads 156 or spaced apart from the first and last beads 156. The beads 156 can serve as a rigid bearing, and in some embodiments advantageously allow the suture 106 to slide, stretch, or otherwise move within the overmolded segment 150. The beads 156 allow the suture 106 to remain flexible due to the discrete nature of the beads 156.

Figure 11D:
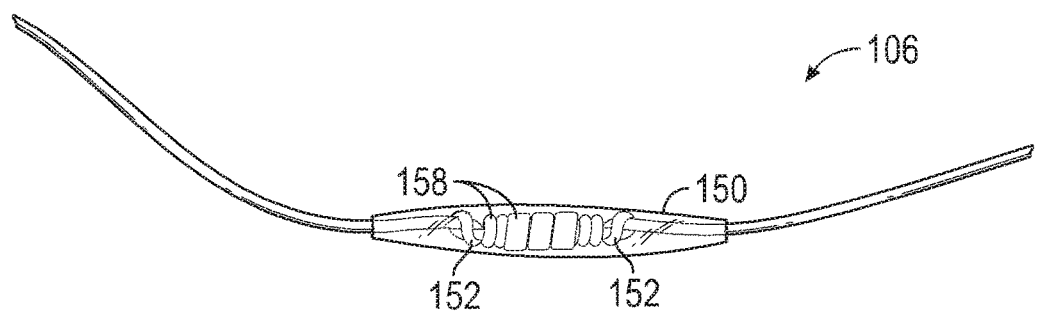

FIG. 11D shows a suture 106 with a series of beads 158. The beads 158 can have varying diameters as illustrated in FIG. 11D. The beads 158 can be formed from a suitable material (e.g., glass). The suture 156 can have similar characteristics as suture 158. The beads 158 can have different diameters. The diameter of the beads 158 can be selected to accommodate the shape of the overmolded segment 150. The suture 106 can have two differing diameters of beads 158. The smaller diameter beads 158 can be located near the suture ends, and the larger diameter beads 158 can be located between the smaller diameter beads 158, or in a different arrangement.

Figure 11E:
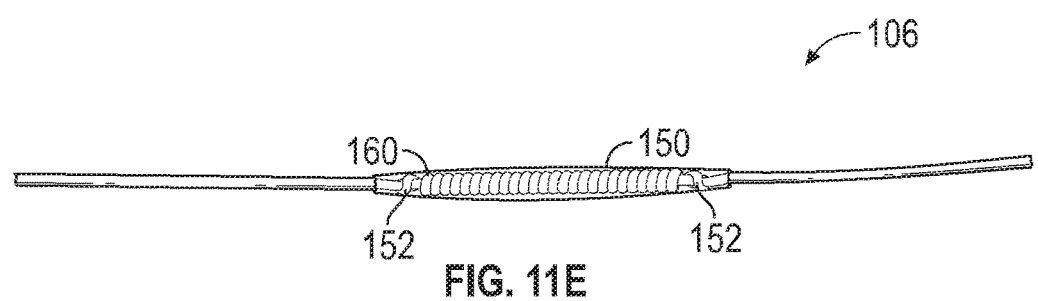

FIG. 11E shows suture 106 with a coil 160. The coil 160 can be formed from a suitable material (e.g., a polymer (e.g., polypropylene), suture, (e.g., #2 or other size monofilament suture), or a metal (e.g., stainless steel)). The coil 160 can be wrapped around the longitudinal suture 106. The coil 160 can be threaded around the longitudinal suture 106. The coil 160 can be retained on the longitudinal suture 106 by knots 152 positioned at the end of the coil 160. The knots 152 can be overhand knots. The knots 152 can be adjacent to the ends of the coil 160 or spaced apart from the ends of the coil 160. The coil 160 can serve as a bearing. The coil 160 can allow the suture 106 to slide, stretch, or otherwise move within the overmolded segment 150. The coil 160 allows the suture 106 to remain flexible. The coil 160 of suture 106 may be more flexible than the beads 156, 158 of sutures shown in FIG. 11C-11D.

Figure 12A:
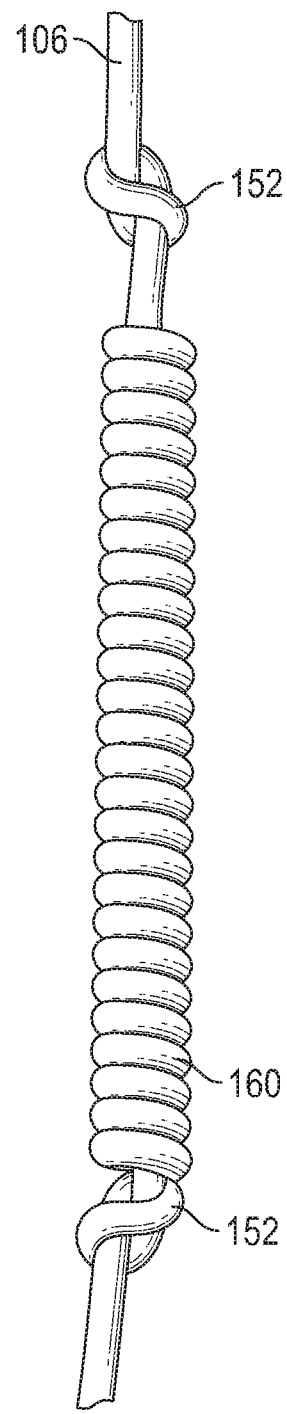
FIGS. 12A-12B illustrate a method of making a suture.
Figure 12B:
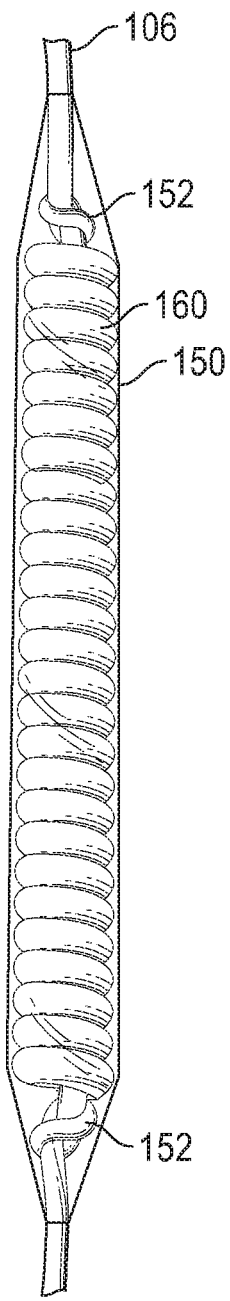
Figure 13A:
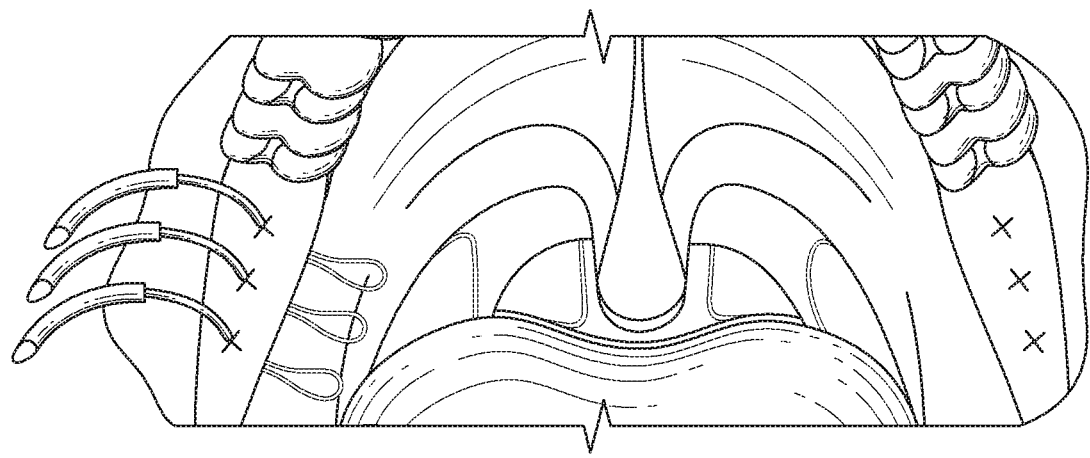
FIGS. 13A-D illustrates a method of delivering a plurality of suture loops into tissue.
Figure 13B:
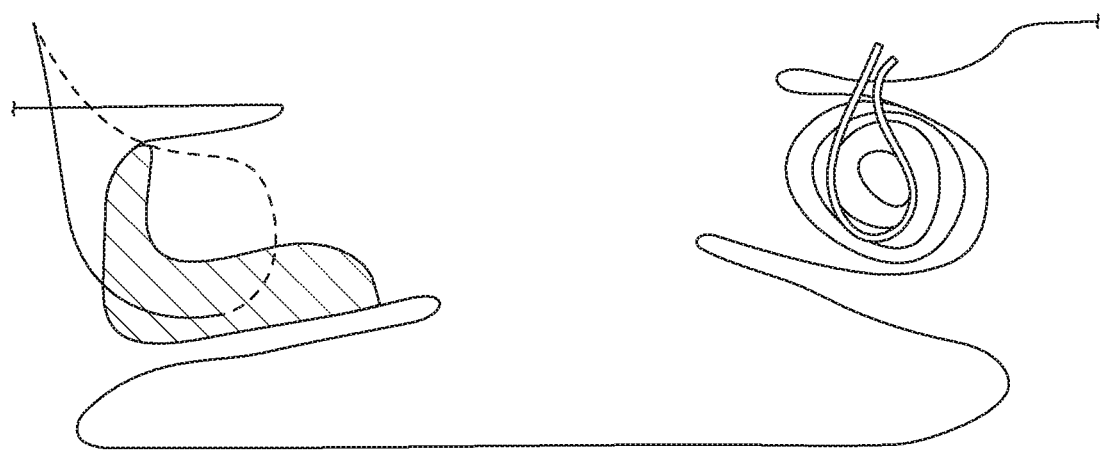
Figure 13C:
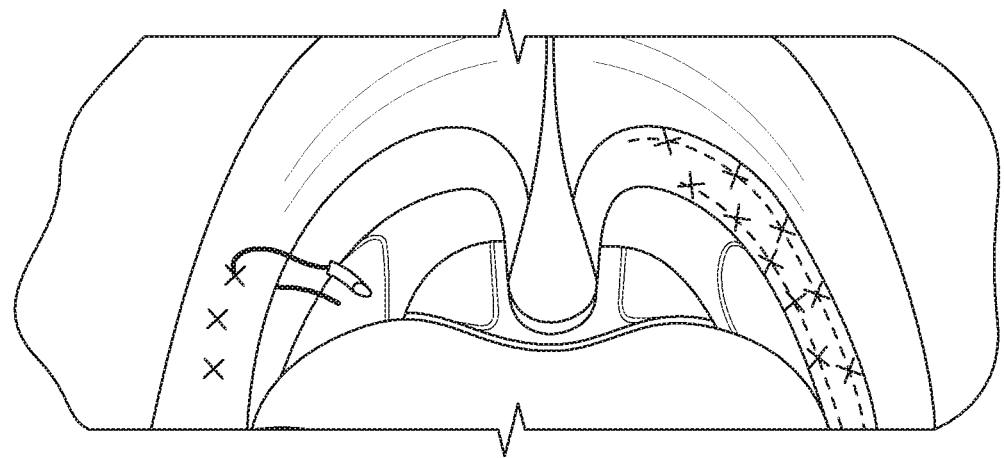
Figure 13D:
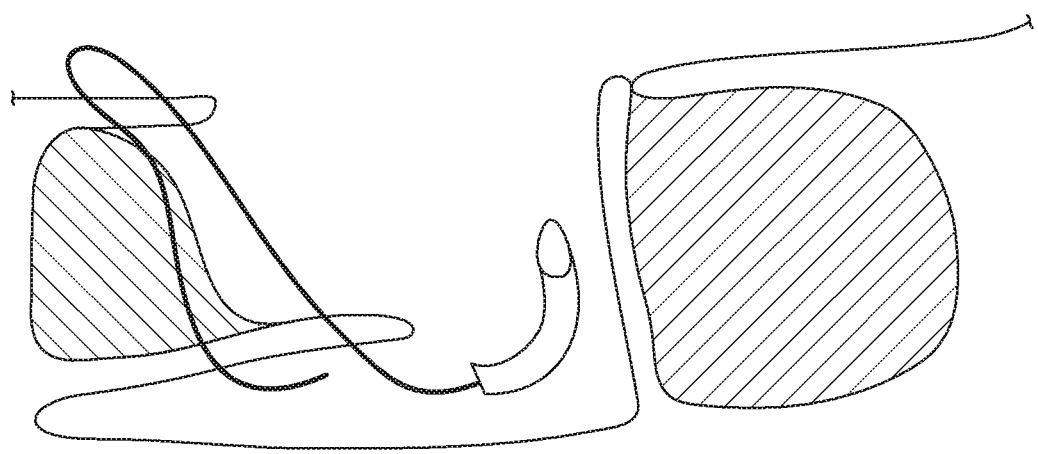

FIG. 12A shows an embodiment of the suture 106 before overmolding. FIG. 12B shows the suture 106 after overmolding, with overmolded segment 150. The length, suture size, and/or overall diameter of the coil 160 can be adjusted depending on the desired clinical result. The coil 160 of suture 106 may be advantageously relatively simple to manufacture. The length, suture size, and/or overall diameter of the overmolded segment 150 can be adjusted depending on the desired clinical result. The overmolded segment 150 of suture 106 may be advantageously relatively simple to manufacture.

In some embodiments, the suture 106 and/or suture 106' could be USP #2, or about 0.020" or less in diameter. In some embodiments, the sections of increased thickness, e.g., the overmolded sections 150, could be between about 0.080" to 0.120", or 0.020" to 0.030"×0.080" to 0.120". In some embodiments, the lengths of the overmolded sections 150 could be between about 2 cm and about 3 cm. The suture 106 with the overmolded section 150 could also include a tapered thickness or diameter section, such as parts of the overmolded sections 150. The length of the taper could be, for example, less than 1 cm, or less than 0.5 cm. In some embodiments, the first suture 106 could be USP #3, or about 0.024" or less in diameter. In some embodiments, the overmolded sections 150 could be between about 0.030" to 0.200", or 0.020" to 0.030"×0.030" to 0.200", or have a diameter that it at least about 20%, 30%, 40%, 50%, 60%, 75%, 100%, 125%, 150%, 200%, or more larger than that of the underlying suture 106 without overmolding. In some embodiments, the lengths of the overmolded sections 150 could be between about 1 cm and about 5 cm. The length of the taper on either side of the overmolded section 150 or largest diameter/thickest section could be up to about 20%, 30%, 40%, or 50% of the length of the overmolded section 150 or entire large diameter/thickest section. In some embodiments, additional suture 106 and other features that can be used or modified for use with embodiments disclosed herein can be found, for example, in U.S. patent application Ser. No. 14/020,617 to Feezor et al., which is hereby incorporated by reference in its entirety.

The surface of any of the disclosed sutures may be mechanically, chemically, or otherwise modified to improve adhesion with, for example, muscle cells and other tissues of the genioglossus. Mechanical modifications create improved adhesion by modifying the surface texture of the implant and may be achieved as part of the manufacturing process and may involve the removal of material from, or the addition of material to the surface of the implant. Chemical adhesion may be achieved through the incorporation of chemical (including biological) compounds into the surface or the bulk material or materials that makes up the implant in order to improve the affinity between cellular components and the implant. Compounds may include, but are not limited to proteins, peptides, antibodies, growth factors, or other molecules which create an affinity for cellular or tissue components.

FIGS. 13A-13D illustrate a method of narrowing the lateral pharyngeal wall. Some surgical procedures indirectly tension the lateral pharyngeal wall. The technique involves a plurality, e.g., two, three, or more suture passes around the superior pharyngeal constrictor muscle. The sutures are sewn into the palatoglossal muscle and tied off as shown. The aforementioned technique can require exposure of muscle with several incisions in the mucosa layer, and the technical ability to consistently anchor the suture in the superior pharyngeal constrictor muscle. The technique can also require the ability to consistently anchor the suture in the palatoglossal muscle. In some cases, there may be increased pain and recovery time for patients due to the mucosal incisions.

Figure 14:
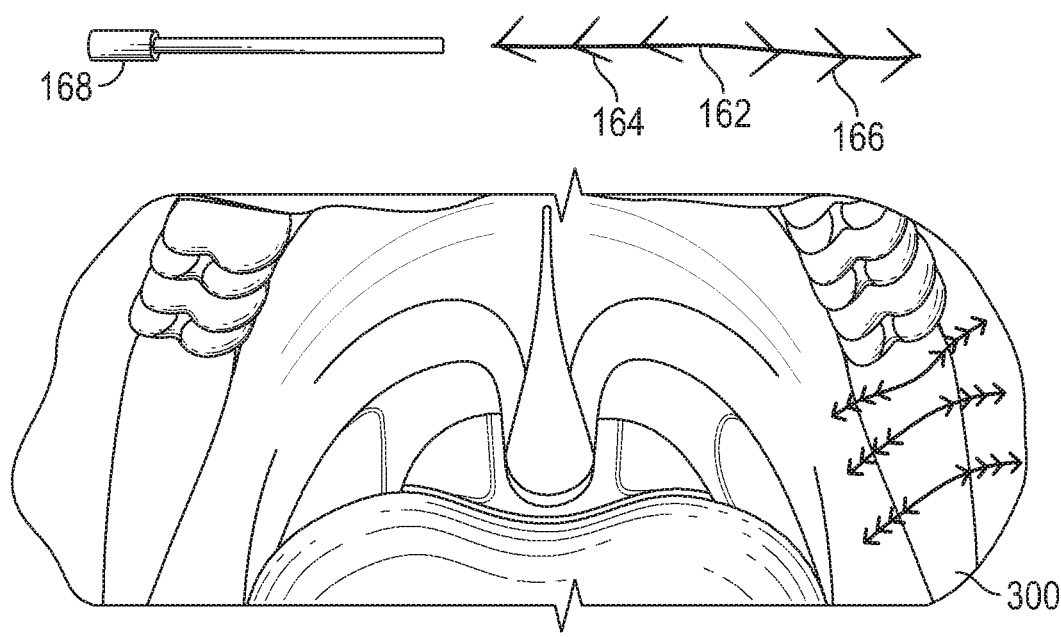
FIG. 14 illustrates a method of narrowing the lateral pharyngeal wall, according to one embodiment of the invention.

In some embodiments, as illustrated in FIG. 14, a barbed implant 162 can be utilized. The barbed implant 162 can include a first end 164 and a second end 166. The first end 164 can include one or more barbs. The second end 166 can include one or more barbs. The barbs on the first end 164 can point in a first direction away from the second end 166. The barbs on the second end 166 can point in a second direction away from the first end 164. In other embodiments, the barbs can point in the same direction. The barbed implant 162 can have a longitudinally extending portion between the first end 164 and the second end 166. In some embodiments, the longitudinally extending portion does not include barbs as shown in FIG. 14. In other embodiments, the longitudinally extending portion includes barbs. The barbed implants 162 can be elastic or inelastic. The longitudinally extending portion can be elastic or inelastic. The barbs can generally move in one direction (e.g., to be inserted into tissue). The barbs resist movement in an opposite direction (e.g., to prevent back out of the barbed implant 162).

The system can include one or a plurality (e.g., about or at least about 2, 3, 4, 5, 6, or more) of barbed implants 162. The barbs can function as proximal and/or distal anchors. The barbed implant 162 can be implanted into tissue 300. The barbed implant 162 can be horizontally oriented within the body of the patient. The method of use can include an implant inserter tool 168. The implant inserter tool 168 can include a proximal handle, an elongate shaft, and a distal tip. The barbed implant 162 can be implanted by advancing an implant inserter tool 168 in a generally horizontal orientation. The implant inserter tool 168 can release the barbed implant 162 into the tissue 300. In some embodiments, the barbed implants 162 could be implanted within about 10 degrees of the horizontal axis. However, in other embodiments, the barbed implants 162 could be within less than about 15 degrees, 30 degrees, 45 degrees, 60 degrees, 75 degrees of the horizontal axis. This provides more localized control of tissue suspension, depending on the desired clinical result.

In some methods of use, a combination of generally horizontally-oriented barbed implants 162 can be used as shown in FIG. 14. In some methods of use, a combination of generally horizontally oriented barbed implants 162 and generally vertically-oriented barbed implants 162 can be used. In some methods of use, a combination of generally vertically-oriented barbed implants 162 can be used. In some embodiments, the distance between barbed implants 162 could be irregular or regular. The distance between the midlines of the barbed implants 162 could be, for example, between about 0.1 cm and about 3 cm. The barbed implants 162 can have the same or different orientations within the tissue 300. In some instances where additional suture strength is required at a single location within tissue, the multiple barbed implants 162 may share a midline axis, but be oriented differently (from −90 to +90 degrees) from each other.

FIG. 14 illustrates three barbed implants 162 deployed in the tissue 300. As shown, the barbed implants 162 are used to tack the superior pharyngeal constrictor muscle to the palatoglossal muscle. The barbed implants 162 may extend from the palatoglossal arch to the palatopharyngeal arch. The barbed implants 162 may each include a longitudinal extending section, the first end 164 and the second end 166, as described herein. The barbs of the first end 164 may be oriented the same as, or differently from the barbs on the second end 166. The barbs on the first end 164 may be opposite the orientation of the barbs on the second end 166. The barbs may be configured to engage tissue 300 when tensioned from different directions.

Figure 15A:
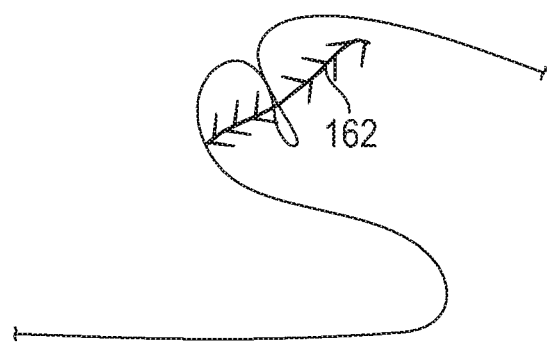
FIGS. 15A-15B illustrate the anatomy with and without an implant.
Figure 15B:
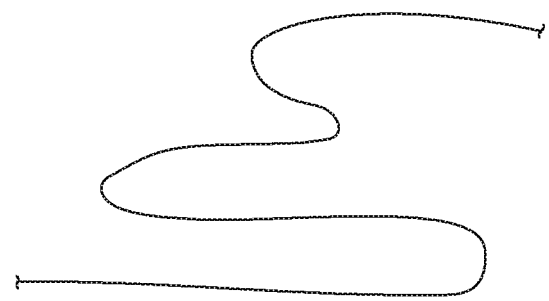

FIGS. 15A-15B illustrates a cross-sectional view of the palatoglossal arch and the palatopharyngeal arch. FIG. 15A shows the barbed implant 162 deployed. The barbed implant 162 compresses the palatopharyngeal arch toward the palatoglossal arch. FIG. 15B illustrates a cross-sectional view of the anatomy without the barbed implant 162. The barbed implant 162 can be deployed at an angle relative to the horizontal. The angle may be approximately 45 degree. The angle can be determined by the relative anatomy of the patient.

Figure 16A:
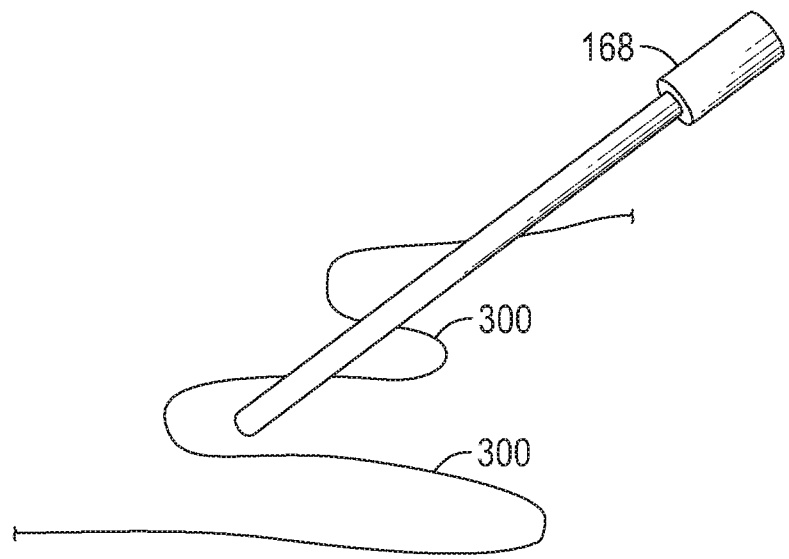
FIGS. 16A-16D illustrate an embodiment of a method of inserting an implant.
Figure 16B:
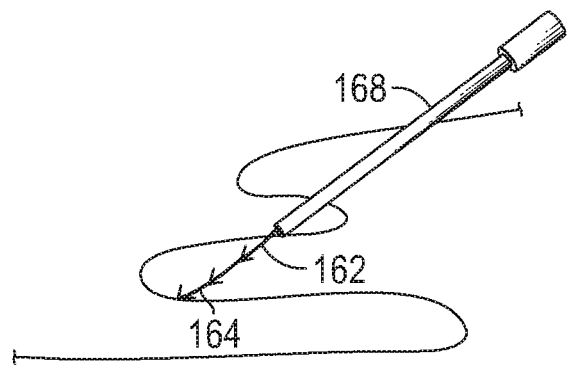

FIGS. 16A-D illustrate a method of inserting the barbed implant 162. FIG. 16A shows the implant inserter tool 168 having the proximal handle, the elongate shaft, and the distal tip. The implant inserter tool 168 can be inserted into and extends between the palatoglossal arch and the palatopharyngeal arch. The implant inserter tool 168 can be advanced until the distal tip is proximate a target location. FIG. 16B shows the barbed implant 162 being deployed from the distal tip of the implant inserter tool 168. This can be accomplished, for example, by actuating a control on the proximal handle to actuate a pushrod distally, for example to expel the barbed implant 162. The first end 164 of the barbed implant 162 engages tissue 300 of the palatopharyngeal arch. In some embodiments, the barbs may further embed in the tissue 300 as a force is applied to the barbed implant 162. The barbs of the barbed implant 162 dig into or otherwise embed in the soft tissue 300. The tool 168 is retracted from the palatopharyngeal arch.

Figure 16C:
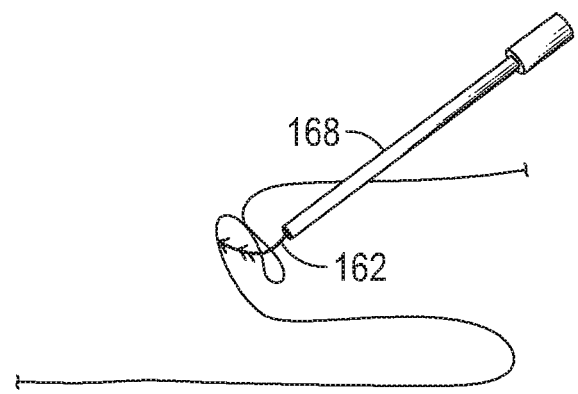

FIG. 16C shows the tool 168 being retracted to the palatoglossal arch. By applying a force (e.g., tension) on the barbed implant 162, the barbs may further embed in the tissue 300. The palatopharyngeal arch may be brought toward the palatoglossal arch. The palatopharyngeal arch may be compressed against the palatoglossal arch. In some embodiments, the palatopharyngeal arch may touch the palatoglossal arch. The palatopharyngeal arch may be pulled laterally and/or anteriorly.

Figure 16D:
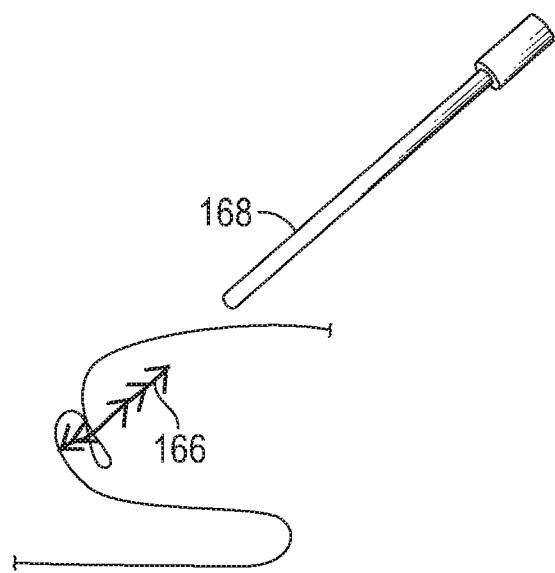

FIG. 16D shows the implant inserter tool 168 being retracted from the palatoglossal arch. The second end 166 of the barbed implant 162 engages tissue 300 of the palatoglossal arch. The barbed implant 162 may be deployed such that the first end 164 engages the palatopharyngeal arch and the second end 166 engages the palatoglossal arch. As force is applied to the barbed implant 162, the barbs may further embed into the soft tissue 300, thereby inhibiting further movement of the barbed implant 162. The method steps shown in FIGS. 16A-16D can be repeated to deploy one or more barbed implants 162 on one or more sides of the airway.

In some cases, the method can include several advantages depending on the desired clinical result. The technique can leave the mucosa layer intact. The barbed implants 162 can be anchored to a larger tissue area than the sutures, in some embodiments. The technique is a simple, repeatable process providing dependable results. The technique may produce a large clinical benefit for minimally invasive intervention.

Figure 17A:
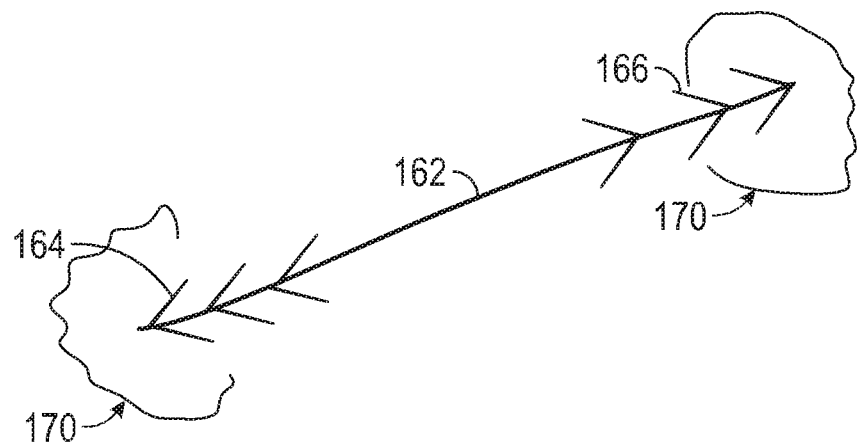
FIGS. 17A-17B illustrate an embodiment of an implant with a tissue ingrowth portion.
Figure 17B:
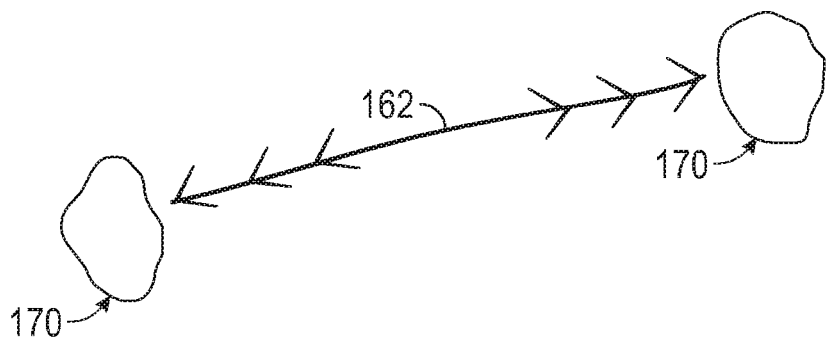

FIGS. 17A-17B illustrate embodiments of the barbed implant 162 with tissue ingrowth material 170. The tissue ingrowth material 170 may be located near the first end 164. The tissue ingrowth material 170 may be located near the second end 166. The tissue ingrowth material 170 may be located near the first end 164 and near the second end 166. The tissue ingrowth material 170 may be located beyond the first end 164. The tissue ingrowth material 170 may be located beyond the second end 166. The tissue ingrowth material 170 may be located beyond the first end 164 and beyond the second end 166. The tissue ingrowth material 170 may provide long-term stability of the barbed implant 162. The tissue ingrowth material 170 may prevent migration of the barbs out of the tissue. The tissue ingrowth material 170 can be biocompatible, to prevent rejection of the barbed implant 162 by the body of the patient. The tissue ingrowth material 170 and may include one or more drugs or other therapeutic agents.

Figure 18A:
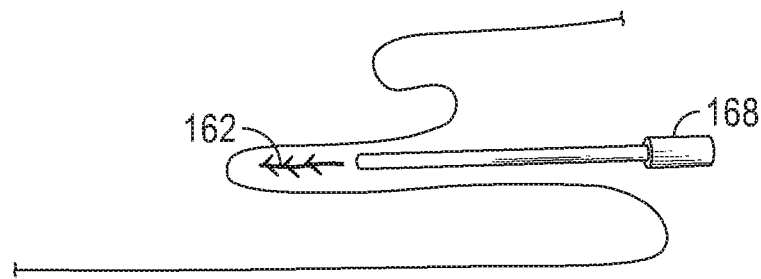
FIGS. 18A-18B illustrate an embodiment of a method of inserting an implant.
Figure 18B:
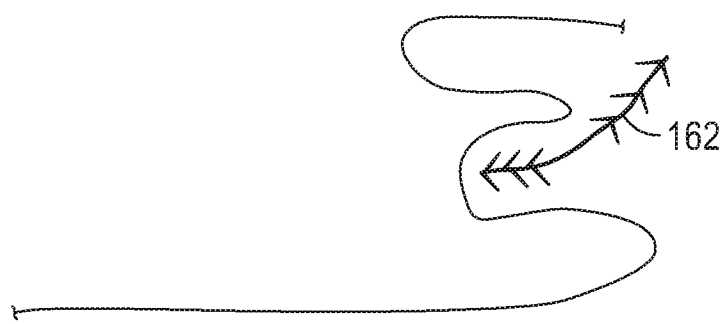

FIGS. 18A-18B illustrate a method of inserting the barbed implant 162. FIG. 18A shows the implant inserter tool 168 inserted into the palatopharyngeal arch. The implant inserter tool 168 is advanced until the distal tip is located at a target location. FIG. 18A shows the barbed implant 162 being deployed from the distal tip of the implant inserter tool 168. The barbed implant 162 engages tissue 300 of the palatopharyngeal arch. In some embodiments, the barbs may further embed in the tissue as a force is applied to the barbed implant 162. The barbs of the barbed implant 162 dig into or otherwise embed in the soft tissue. The implant inserter tool 168 is retracted from the palatopharyngeal arch. FIG. 18B shows the implant inserter tool 168 retracted. The barbed implant 162 spans from the palatopharyngeal arch to the base of the palatoglossal arch. The barbed implant 162 compresses the palatoglossal arch. By applying a force (e.g., tension) on the barbed implant 162, the barbs may further embed in the tissue. The palatopharyngeal arch may be brought toward the palatoglossal arch. The palatopharyngeal arch may be pulled laterally. This technique avoids tacking the palatopharyngeal arch directly to the palatoglossal arch.

Figure 19A:
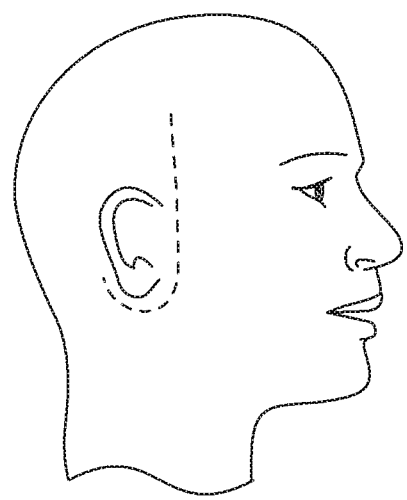
FIGS. 19A-19E illustrate an embodiment of a method of inserting a suture.
Figure 19B:
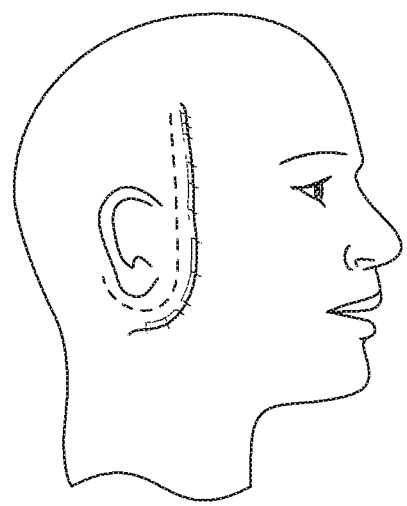
Figure 19C:
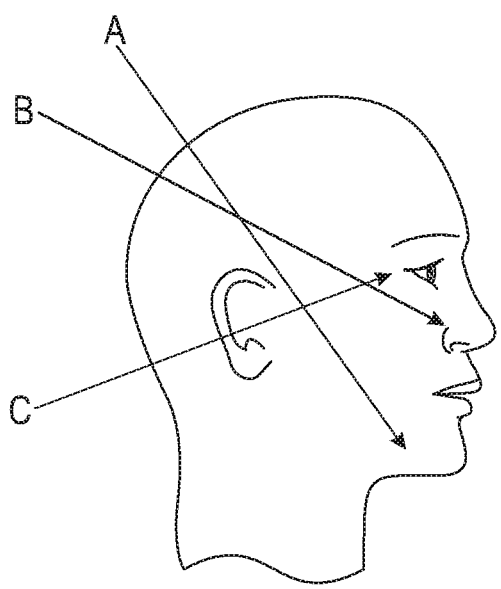
Figure 19D:
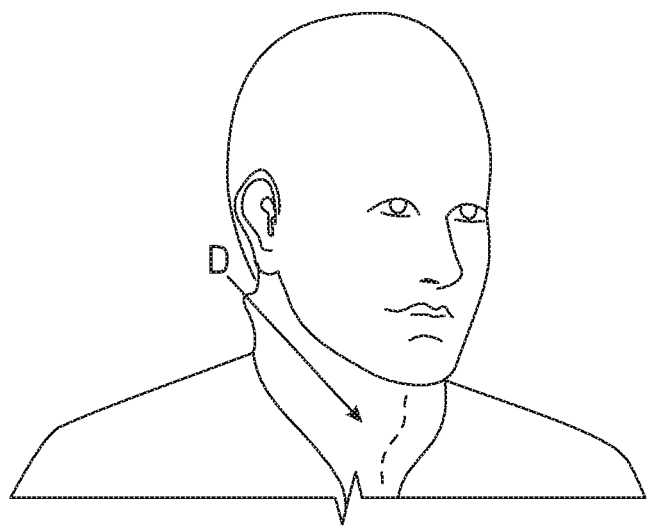
Figure 19E:
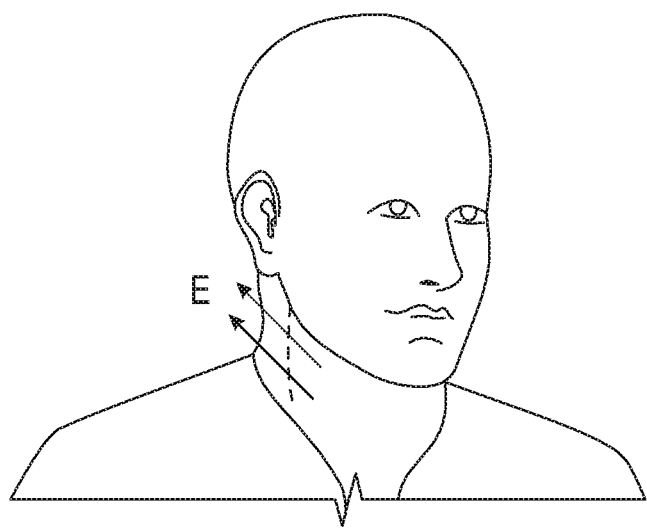

FIGS. 19A-19E illustrate a method of inserting a suture 106 for a tissue lift procedure. The suture 106 can include the overmolded segment 150 as described herein. FIG. 19A shows the method step of making an incision in the skin of the head of a patient. FIG. 19B shows the method step of making a small surgical dissection pocket. FIGS. 19C-19E show various non-limiting possible suture passes. Path A provides neck lift, Path B provides mid-level cheek lift, and Path C provides eye line lift, as shown in FIG. 19C. Path D, as shown in FIG. 19D, shows the path wherein the suture passes inferiorly to the mandible. The suture is advanced until reaching the midline of the neck. The method may include the step of placing suspension sutures such as suture 106 with the overmolded segment 150 under the jaw line. Path E, as shown in FIG. 19E illustrates the path of suture 106 forming loops in the neck. The method may include the step of suspending a suture, trimming extra skin, and/or closing the incision. The sutures may be placed using the SMAS, or the sub-muscular aponeurotic system. The system and methods, such as the use of various suture passers, can be as disclosed herein and can be, or modified from systems and methods described in U.S. Pat. No. 8,460,322, the entire disclosure of which is incorporated by reference.

FIG. 20 illustrate a method of inserting a suture 106. The suture 106 can include the overmolded segment 150 as described herein. The methods can be performed by a suture passer described herein and in commonly owned U.S. Pat. No. 8,460,322, the entire disclosure of which is incorporated by reference. The suture passer can be modified, (e.g., reduced in size). The suture passer can be used to place suture 106. The suture 106 can form loops within the tissue instead of single short sections of suture. The suture passer can place suture 106 into the superior pharyngeal constrictor muscle. The suture 106 can be placed as shown. The suture 106 can be placed near the palatopharyngeal arch, the palatoglossal arch and/or any location between the palatopharyngeal arch and the palatoglossal arch. The suture 106 can be anchored. The suture 106 can be anchored into palate tissue and/or the hard palate. The suture 106 can be tensioned to stabilize the lateral pharyngeal wall. The method can in some embodiments narrow the lateral pharyngeal wall and/or provide the lateral pharyngoplasty.

FIGS. 21A-21B illustrate a method of using one or more bone anchors 172 in an adjustable tensioning system. The bone anchors 172 can be knotless bone anchors in some embodiments. The suture 106 can be inserted into the bone anchors 172. In some embodiments, the suture 106 includes a first strand 106A, a second strand 106B and an arc connecting the first strand 106A and the second strand 106B. The first strand 106A has a free end and the second strand 106B has a free end. The free ends of the suture 106 can be inserted into a lumen of the bone anchor 172. The bone anchor 172 can be tightened to secure the first strand 106A and the second strand 106B. The bone anchor 172 can be loosened to release the first strand 106A and the second strand 106B and allow for adjustable tensioning without necessarily requiring untying of the suture loop.

The bone anchors 172 can be used to secure the suture 106 within the face or neck, or another desired anatomical location. The suture 106 can form a loop such that the suture arc 106C is disposed within the tissue. The sutures 106 may be placed to provide a face and/or neck lift.

The bone anchor 172 can provide post-operative adjustability to the suture 106. For instance, the suture 106 can be adjusted after the arcs 106C are placed, during the procedure and/or at any time in the future. The suture 106 could be adjusted days, months, or years after the suture 106 is placed within the body. The bone anchor 172 permits adjusting the suture 106 by increasing or decreasing tension in a minimally invasive manner. In some embodiments, the bone anchor 172 can selectively release the first strand 106A. In some embodiments, the bone anchor 172 can selectively release the second strand 106B. In some embodiments, the bone anchor 172 can selectively release the first strand 106A and the second strand 106B. The surgeon can apply tension to the first strand 106A and/or the second strand 106B. Once adjusted, the bone anchor 172 can be tightened to retain the first strand 106A and the second strand 106B. The bone anchor 172 permits adjusting the face and/or neck lift in a minimally invasive manner. The free ends of the suture 106 may be pulled, slid, tensioned and/or manipulated to adjust the suture 106. This movement would then adjust the tissue, bone, and/or skin coupled to the suture 106 (e.g., adjust the face and neck lift).

The bone anchor 172 can have lock and unlock capabilities. The bone anchor 172 can include an opening (e.g., a hexagonal opening) for the insertion of a tool (not shown). The tool can lock and unlock the bone anchor 172, allowing for the suture 106 to be adjusted. The bone anchor 172 may be implanted on a surface of the skin and/or within the body. The bone anchor 172 can be placed above the ear (e.g., in the temporal bone), as shown in FIG. 21A. The bone anchor 172 can be placed under the skin near the ear, as shown in FIG. 21B. The bone anchor 172 placed under the skin can be adjusted by making a small incision near the bone anchor 172. The incision may be near the implantation location for the bone anchor 172. The tool can be inserted into the incision to adjust the bone anchor 172.

Figure 22A:
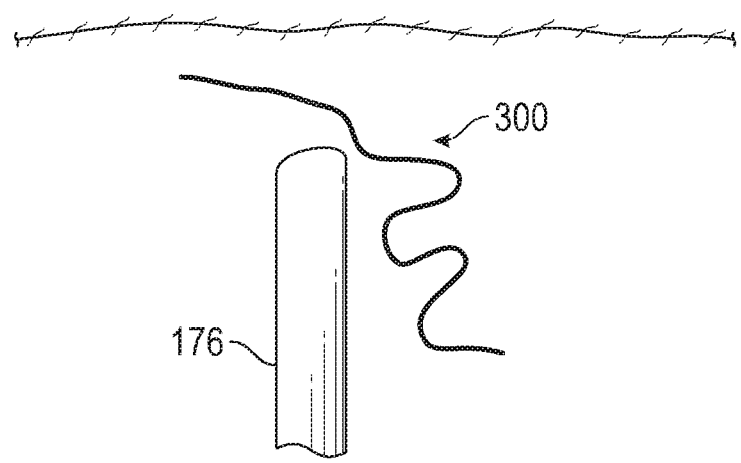
FIGS. 22A-22B illustrate an embodiment of an apparatus and method of securing a tissue.
Figure 22B:
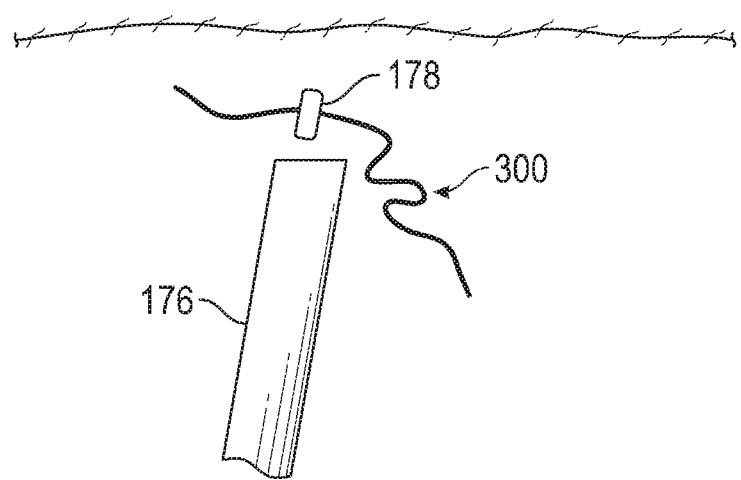

FIGS. 22A-22B illustrate a tool 176 and method for moving the superior pharyngeal constrictor or another desired muscle. The tool 176 can move the superior pharyngeal constrictor muscle in any direction (e.g., laterally and/or anteriorly). The tool 176 can stabilize the superior pharyngeal constrictor muscle in the desired location (e.g., laterally and/or anteriorly). The tool 176 can insert a fastener 178 (e.g., a tack, staple, cap, suture loop, or suture). The fastener 178 can be biodegradable or bioabsorbable in some cases. The tool 176 can include a blunt tip for moving the tissue. The tool 176 can couple to the fastener 178 for stabilizing the tissue. FIG. 22A shows the tool 176 moving the superior pharyngeal constrictor muscle laterally. The tool 176 can move the superior pharyngeal constrictor muscle via the blunt tip. The superior pharyngeal constrictor muscle may be moved toward the side of the airway. The tool 176 can be positioned to discharge (e.g., launch, fire) the fastener 178 to stabilize the tissue. The method can be repeated for the contralateral side of the airway to move the superior pharyngeal constrictor muscle laterally.

Figure 23A:
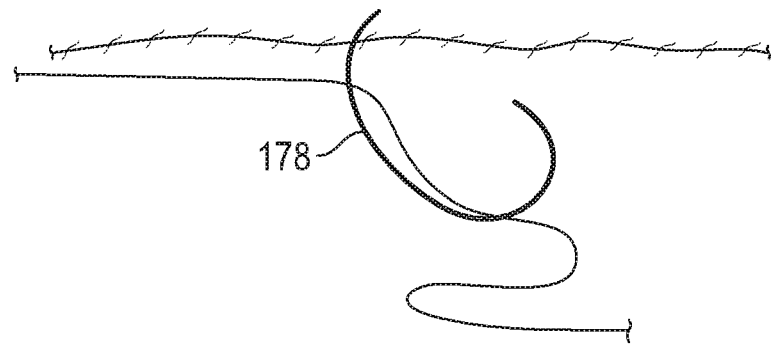
FIGS. 23A-23C illustrate embodiments of a fastener.
Figure 23B:
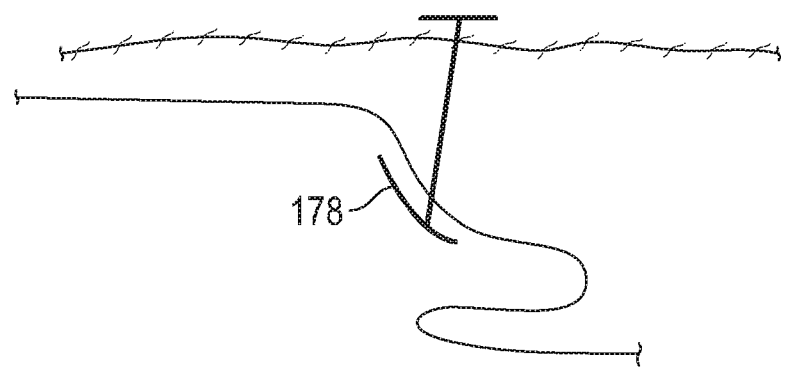
Figure 23C:
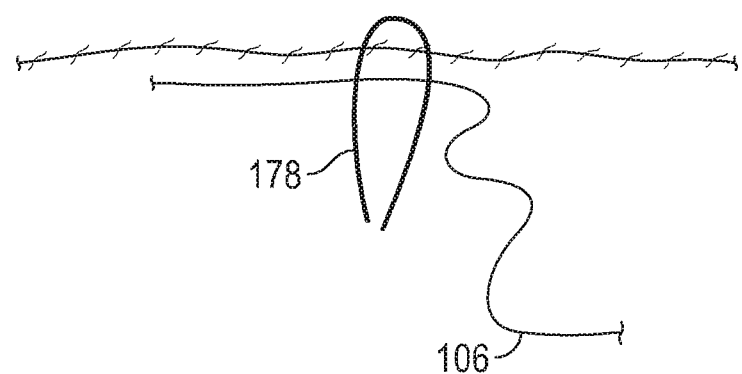

FIGS. 23A-23C illustrate some embodiments of the fastener 178, with the placement of the fastener 178 shown in relation to the superior pharyngeal constrictor muscle. FIG. 23A shows the fastener 178 as a staple, with ends biased toward each other. FIG. 23B shows the fastener 178 as a tack, having a proximal tissue contacting structure and a distal tissue contracting structure, both operably connected to a tension element. FIG. 23C shows the fastener 178 as the suture 106. The suture 106 can form a loop by bringing the first end 106A to the second end 106B. The suture 106 can be stabilized with anchors as described herein. The suture 106 can be placed with a device like a suture passer as described herein. The fastener 178 can be a barbed suture 162, as shown in FIG. 14 for example. The fastener 178 can be bioabsorbable in some embodiments. The fastener 178 can extend from the superior pharyngeal constrictor muscle to a location near the palatopharyngeal arch, the palatoglossal arch and/or any location between the palatopharyngeal arch and the palatoglossal arch. The fastener 178 can extend from the fascia behind the superior pharyngeal constrictor muscle.

Figure 24A:
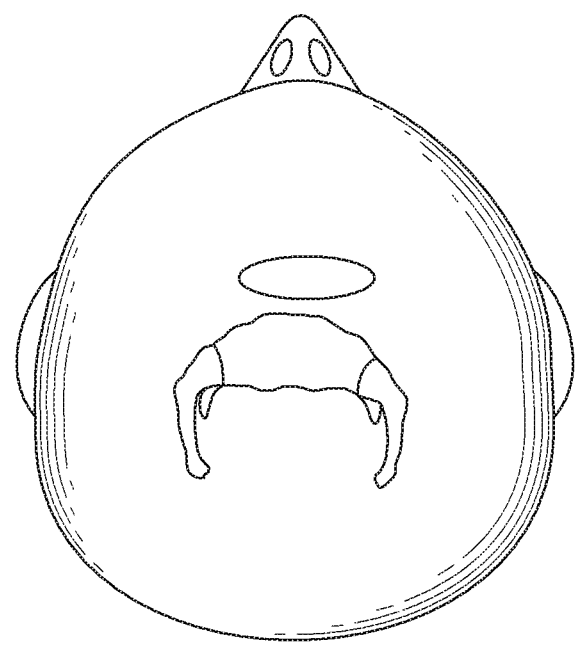
FIGS. 24A-24D illustrate an embodiment of a method of hyoid bone suspension.

FIGS. 24A-24D illustrate a method of hyoid suspension. The hyoid bone is located in the anterior midline of the neck and is anchored by muscles. The hyoid aids in tongue movement and swallowing. Hyoid suspension involves pulling the hyoid forward in order to increase the size of the airway. FIG. 24A illustrates the method step of forming an incision in the neck of a patient. The incision can be, for example, between 2 cm and 4 cm. The incision may extend from, for example, the hyoid bone to the mandible. The surgeon can dissect the tissue and muscle to reach the hyoid bone.

Figure 24B:
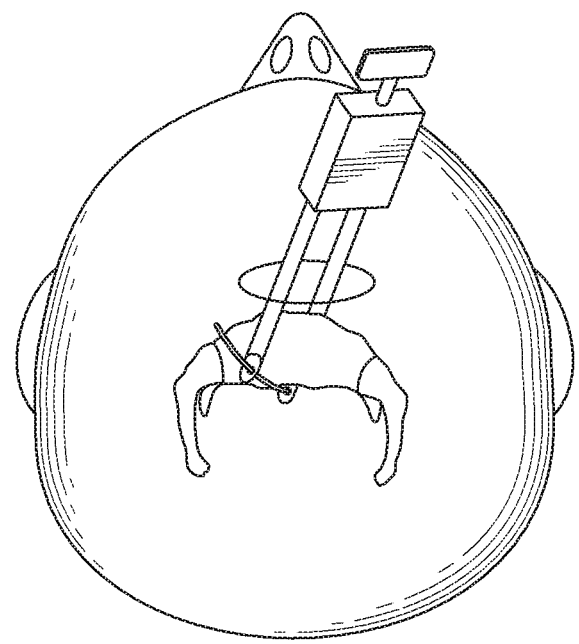

FIG. 24B illustrates the method step of using a suture passer for hyoid suspension. The method may utilize a suture passer substantially similar to the systems and methods described herein or in commonly owned U.S. Pat. No. 8,460,322, the entire disclosure of which is incorporated by reference. The suture passer can be used to pass a suture loop 106 around the body of the hyoid bone. The suture 106 can include the overmolded segment 150. The suture 106 has the first strand extending longitudinally 106A, the second strand extending longitudinally 106B, and the arc 106C connecting the first strand 106A and the second strand 106B. The arc 106B is passed around the hyoid bone. The suture loop 106 can be elastic or inelastic. The suture 106 can be substantially similar to the sutures described herein, including the sutures shown in FIGS. 11A-12B. The arc 106C can be on one side of the hyoid bone. The first 106A and second strand 106B can be on the other side of the hyoid bone. In some methods, the first strand 106A and the second strand 106B are then passed around the hyoid bone. The first strand 106A and the second strand 106B are passed under the arc 106B. The suture 106 can form a girth hitch. Other knot configurations are contemplated. For instance, the suture 106 could be wrapped around the hyoid bone forming a klemhiest or prusik knot.

The first suture 106 can be replaced with a second, larger suture 108. The larger suture 108 can include be a larger diameter suture, suspension loop, suture tape, etc. The larger suture 108 can be similar to suture 106. The larger suture 108 can prevent erosion through the bone. The second, larger suture 108 can be elastic. The larger suture 108 can include the overmolded segment 150 as described herein. The suture 108 has a first strand extending longitudinally 108A, a second strand extending longitudinally 108B, and an arc 108C connecting the first strand 108A and the second strand 108B.

In some methods of use, the first strand 106A is passed around the hyoid bone. The arc 106C can be in contact with the hyoid bone. The second strand 106B can be on the other side of the hyoid bone. The suture 106 can be used to place the suture 108, akin to a guide suture. In some methods, the arc 108C can be placed around the first strand 106A. The arc 108C can be operably coupled to the first strand 106A. The suture 106 can be pulled. In some embodiments, the second strand 106B of the suture 106 is pulled. The arc 108C can be on one side of the hyoid bone. The first 108A and second strand 108B can be on the other side of the hyoid bone. In some methods, the first strand 108A and the second strand 108B are then passed around the hyoid bone. The first strand 108A and the second strand 108B are passed under the arc 108B. The suture 108 can form a girth hitch. Other knot configurations are contemplated. For instance, the suture 108 could be wrapped around the hyoid bone forming a klemhiest or prusik knot.

Figure 24C:
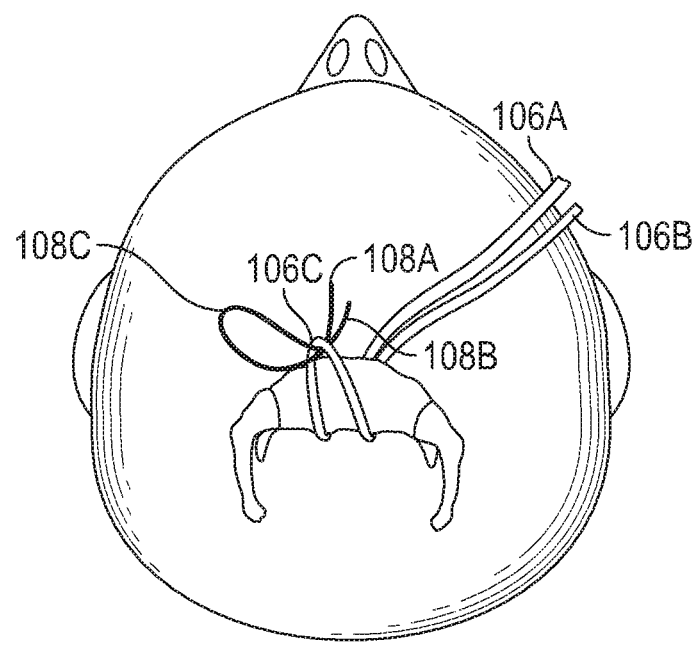

In some methods of use, the arc 106C is passed around the hyoid bone as shown in FIG. 24C. The arc 106C is on one side of the bone and the first strand 106A and the second strand 106B can be on the other side of the hyoid bone. In some methods, the arc 108C can be placed under the arc 106C. The suture loop 106 can be pulled. In some embodiments, the first strand 106A and the second strand 106B of the suture 106 are pulled. The arc 108C can be on one side of the hyoid bone. The first 108A and second strand 108B can be on the other side of the hyoid bone. In some methods, the first strand 108A and the second strand 108B are then passed around the hyoid bone. The first strand 108A and the second strand 108B are passed under the arc 108B. The suture 108 can form a girth hitch. Other knot configurations are contemplated. FIG. 24C shows the method of pulling the larger suture 108, which can be operably connected to the smaller guide suture 106 in some embodiments.

Figure 24D:
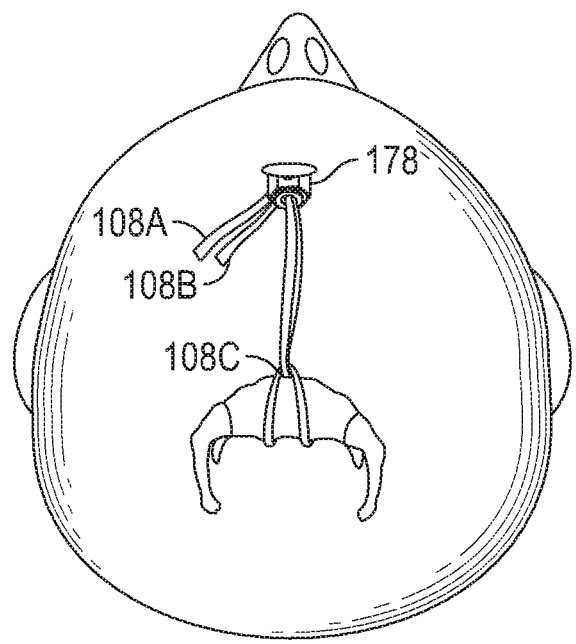

FIG. 24D illustrates the method step of securing the suture 106 and/or larger suture 108 to the mandible. The method may utilize a bone anchor 178, which can include any or all of the features of bone anchor 178 described herein. The bone anchor 178 can be a knotless bone anchor. The bone anchor 178 can be a locking bone screw. The loop of the suture 106 and/or larger suture 108 provides a knotless attachment to the hyoid bone.

The tension, position, and/or suspension of the hyoid bone can be adjusted by adjusting the loop of the suture 106 and/or larger suture 108. For instance, pulling on the first strand 106A and/or the second strand 106B can change the position of hyoid bone. For instance, changing the location of the suture 106 relative to the hyoid bone can change position of the hyoid bone.

The bone anchor 178 can allow for post-operative adjustment of the suture 106 and/or larger suture 108. The bone anchor 178 can release the first strand 108A and or the second strand 108B. The surgeon can adjust the tension provided by the first strand 108A and the second strand 108B. The larger suture 108 can be adjusted after the knot is placed, and/or at any time in the future. The larger suture 108 could be adjusted days, months, years after the larger suture 108 is placed within the body. The larger suture 108 can be adjusted acutely or chronically. The method of passing the suture 106, 108 around the hyoid bone may be simpler, easier, and more minimally invasive than using a curved needle. Although FIG. 24D shows one larger suture 108, more than one larger suture 108 can be utilized (e.g., two girth hitch knots, three girth hitch knots, etc.). The thickness, strength, and/or other material properties may be selected to minimize the number of larger sutures 108. A single larger suture 108 of a sufficiently thick and/or strong material may be able to stabilize the hyoid bone with respect to the mandible.

Figure 25A:
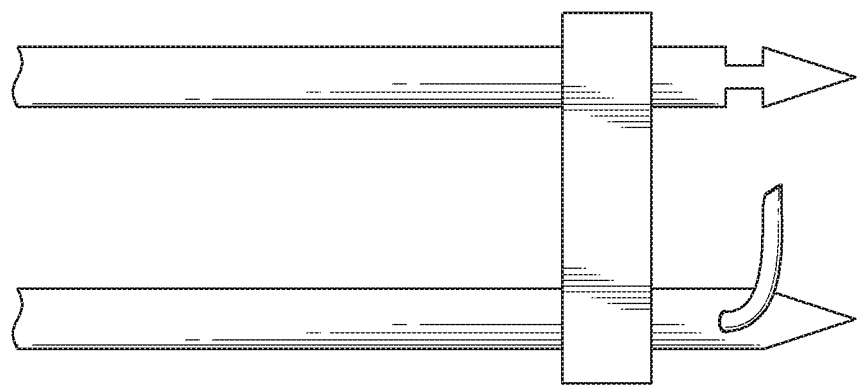
FIGS. 25A-25B illustrate an embodiment of a suture passer.
Figure 25B:
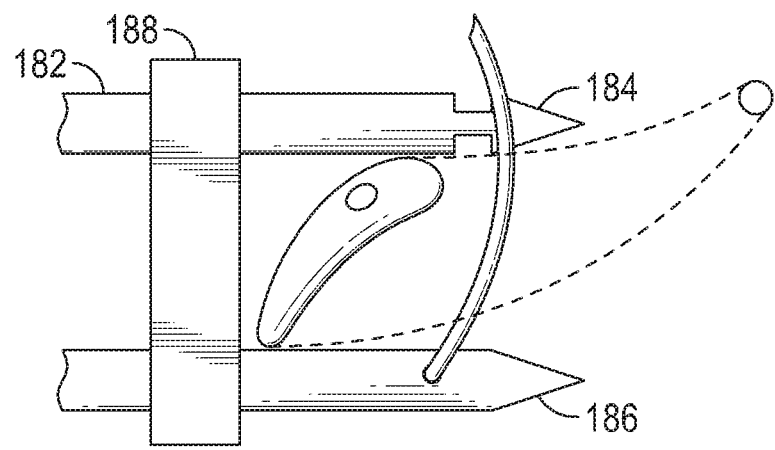

FIG. 25A-25B illustrate a suture passer, in particular the distal end of the suture passer. The suture passer 182 can be modified from the suture passer described in commonly owned U.S. Pat. No. 8,460,322, the entire disclosure of which is incorporated by reference. The suture passer 182 can be modified to include one or more sharpened suture passing needles 184. The sharper needles 184 may be configured for passing through tissues having a greater inherent resistance to puncture, such as ligaments (e.g., hyoepiglottic ligaments, hypothyroid ligaments). The design and/or material of the needle 184 may be selected to enhance stiffness.

The suture passer 182 can be modified to include one or more sharp tips 186. The sharp tips 186 on the ends of the suture passer 182 may be useful in passing through ligaments as noted above. The suture passer 182 can include a depth stop 188 which may limit the forward movement of the suture passer 182. The depth stop 188 may serve as a safety measure, to prevent the suture passer 182 from puncturing the airway. Alternatively, the tips could be blunt and atraumatic in some embodiments.

FIG. 25B illustrates the placement of the suture passer 182 within the body of the patient. The sharp tips 186 may surround the hyoid bone. The needle 184 may penetrate the hyoepiglottic ligament. The needle 184 may extend from one sharp tip 186 to the other sharp tip 186 in order to pass the suture. Surrounding structures such as the hyothryoid ligament, thyroid cartilage, and epiglottis are also shown for reference.

Figure 26A:
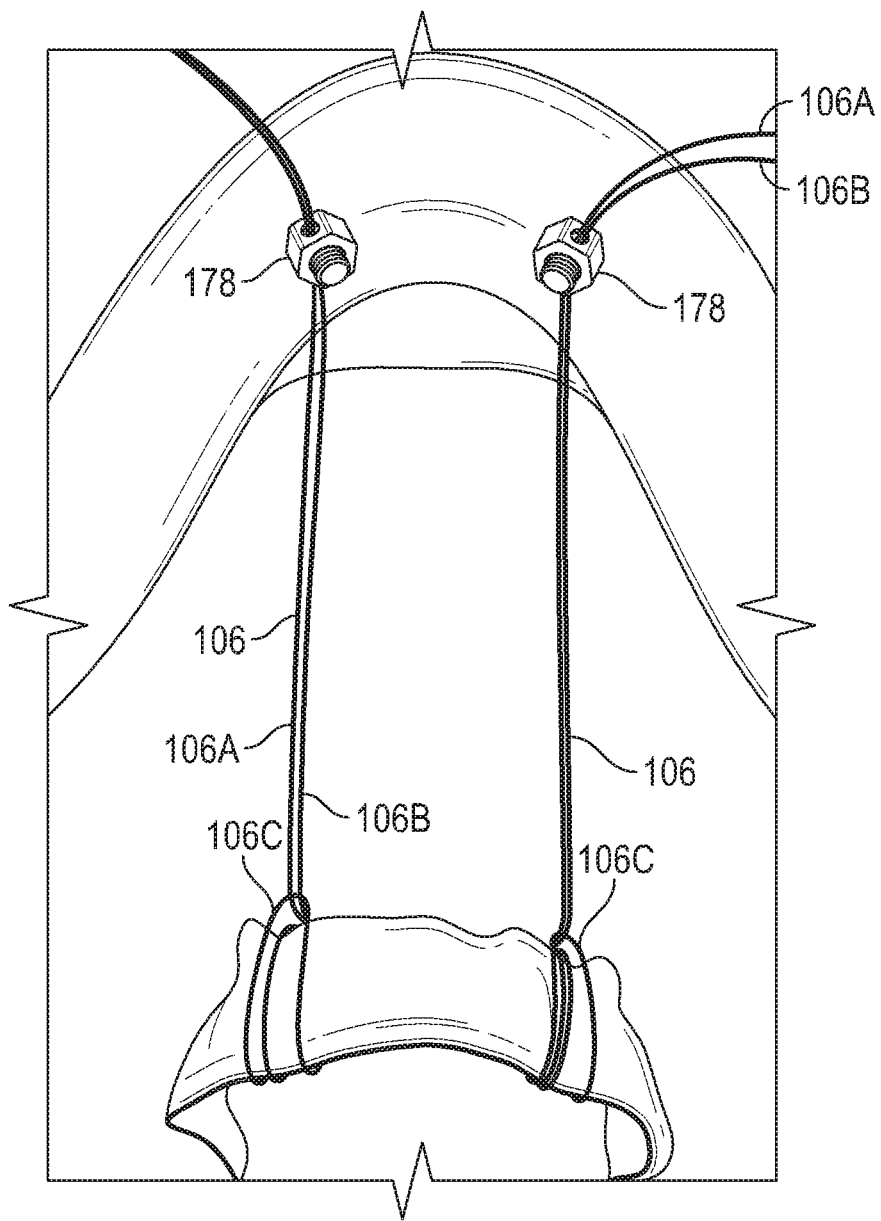
FIGS. 26A-26B illustrate an embodiment of a method of hyoid bone suspension.
Figure 26B:
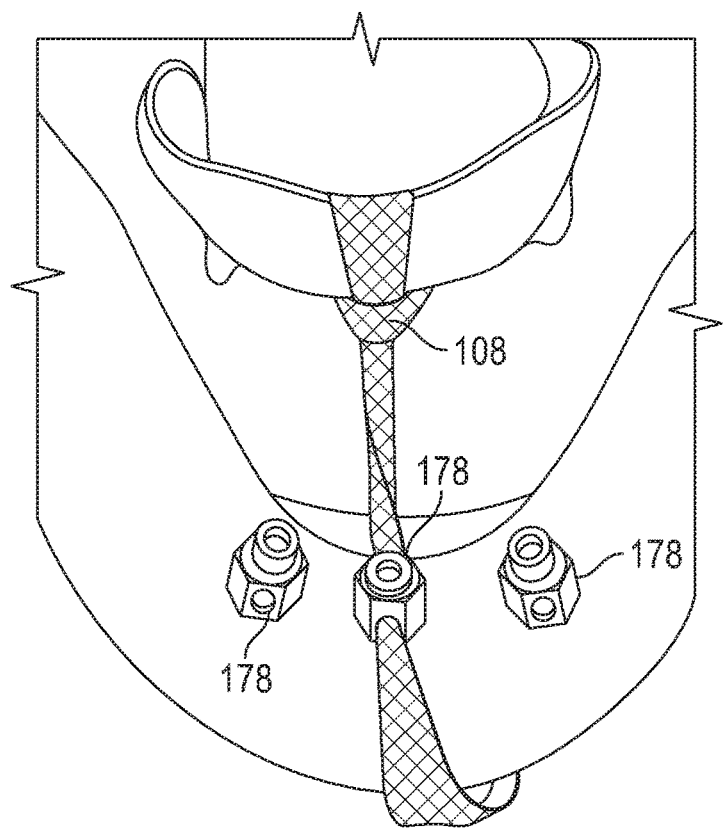

FIG. 26A-26B illustrate a method of hyoid bone suspension. FIG. 26A illustrates the method step of forming a girth hitch around the hyoid bone. FIG. 26A utilizes two sutures 106 (e.g., #2 suture, suture tape (e.g., 2 mm suture tape)). One, two, or more girth hitch knots may be utilized as shown in FIG. 26A. The first strand 106A and the second strand 106B pass under the arc 106C. The first strand 106A and the second strand 106B of the suture 106 are secured to a bone anchor 178. The bone anchor 178 can be located on the mandible. The bone anchor 178 can be tightened to securely hold the first strand 106A and the second strand 106B. The bone anchor 178 can be loosened to release the first strand 106A and the second strand 106B. The surgeon can alter the tension applied to the hyoid bone. The bone anchor 178 can be tightened after the adjustment. FIG. 26A shows a configuration with two side-by-side girth hitch knots, and two bone anchors 178. FIG. 26B shows a configuration with one girth hitch knot illustrated using suture tape, and three bone anchors 178. Additional girth hitch knots utilizing sutures 106 may be utilized in FIG. 26B with respect to the remaining bone anchors 178. The ratio of girth hitches or other knots to bone anchors 178 may be greater than 1:1 (2 girth hitches to 1 bone anchors) or equal to 1:1 (2 girth hitches to 2 bone anchors) in some embodiments. The ratio of sutures 106 to bone anchors 178 may be greater than 1:1 (2 girth hitches to 1 bone anchors) or equal to 1:1 (2 girth hitches to 2 bone anchors) in some embodiments.

Figure 27A:
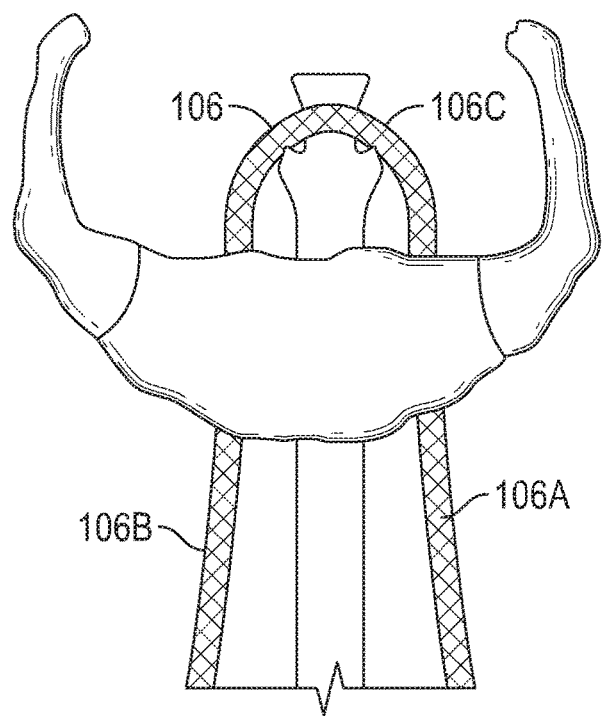
FIGS. 27A-27D illustrate an embodiment of a method of hyoid bone suspension.
Figure 27B:
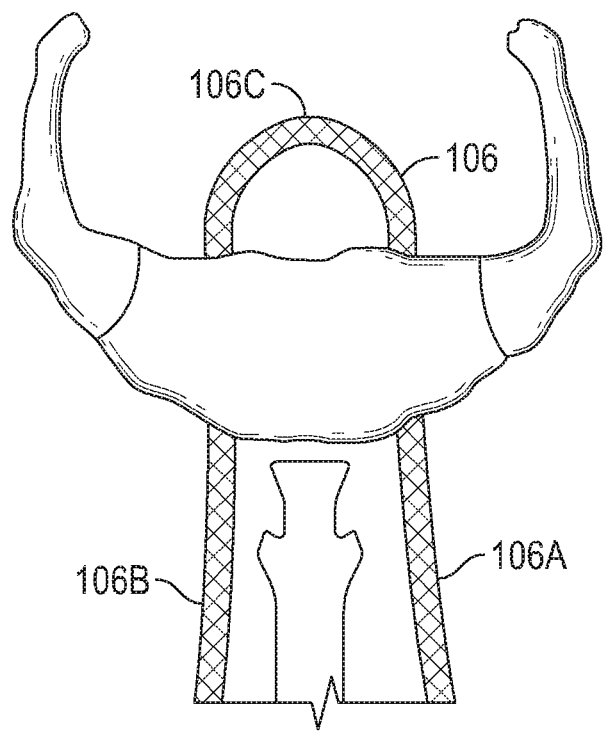
Figure 27C:
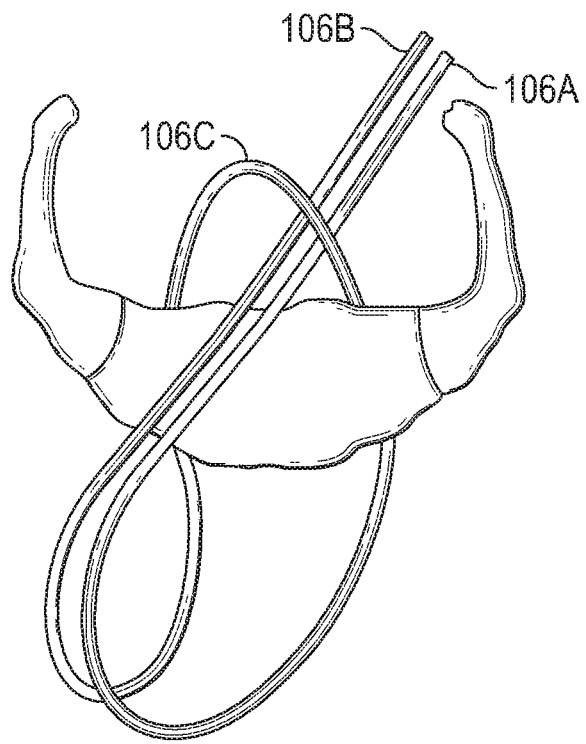
Figure 27D:
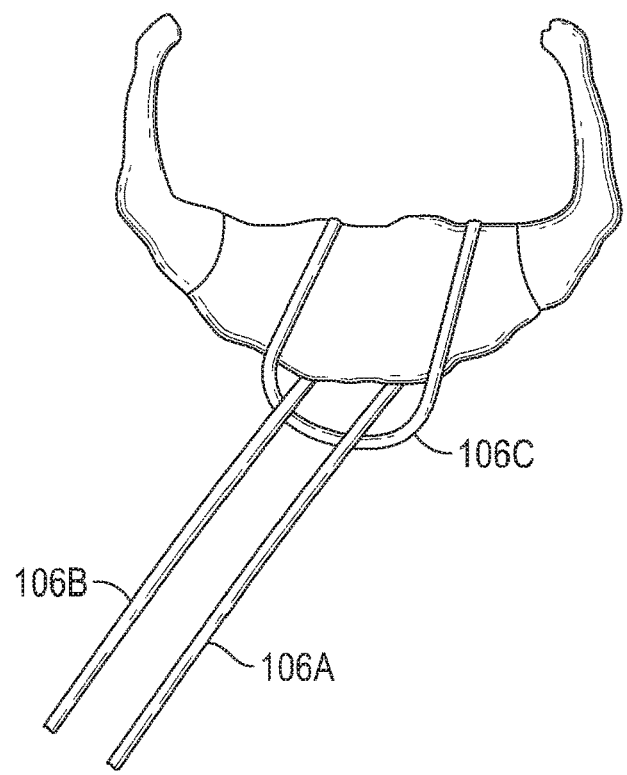

FIG. 27A-27D illustrates a method of forming a girth hitch, in some embodiments. The suture 106 includes the first strand 106A, the second strand 106B, and the arc 106C. FIG. 27A shows the method step of conducting a pass with a suture passer. The suture 106 may be folded, held or otherwise coupled to the suture passer. FIG. 27B shows the method step of retracting the suture passer and/or the needle of the suture passer. The arc 106C remains within the body. FIG. 27C illustrates passing the first strand 106A and the second strand 106B of the suture 106 through the arc 106C of the suture 106 to form a girth hitch. FIG. 27D illustrates the method step of tensioning the first strand 106A and the second strand 106B of the suture 106 to form a girth hitch. The first strand 106A and the second strand 106B of the suture 106 can be coupled to a bone anchor 178 as described herein. The bone anchor 178 can be attached to the mandible. The suture 106 may be either pre-attached to the bone anchor 178 prior to the procedure, or following formation of the girth hitch. The suture 106 can be a smaller diameter guide suture. In some methods, the suture 106 can be coupled with a larger diameter suture 108, which can follow the path of the guide suture 106 to create a girth hitch. In some methods, the arc 108C of the larger diameter suture 108 can be passed under the arc 106C of the suture 106C to create a girth hitch.

The method illustrated in FIG. 27A-27D illustrates the creation of a girth hitch around the hyoid bone at the midline (e.g., near the midline, substantially near the midline). The girth hitch may be connected to a bone anchor 178. The bone anchor 178 may be attached to the mandible at the midline (e.g., near the midline, substantially near the midline).

Figure 28:
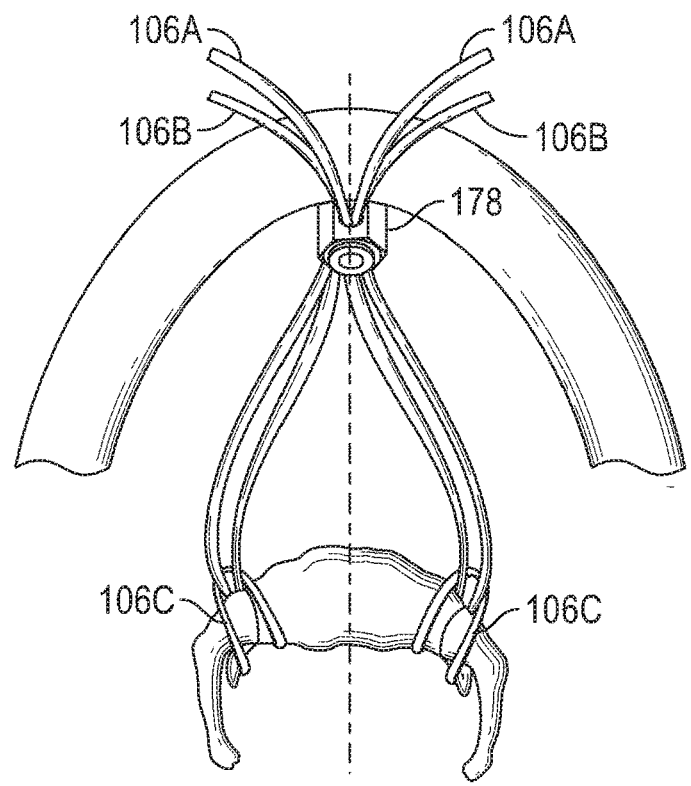
FIG. 28 illustrates an embodiment of a method of hyoid bone suspension.

Alternatively two girth hitch knots may be deployed. The girth hitch knots may be coupled to the hyoid bone. The two girth hitch knots can be around the hyoid bone. The two girth hitch knots can be placed on either side (e.g., right side, left side) of the midline of the hyoid bone, as shown in FIGS. 26A and 28. In some embodiments, the two girth hitch knots can be coupled to two bone anchor 178. The two bone anchors 178 can be placed on either side (e.g., right side, left side) of the midline of the mandible, as shown in FIG. 26A. In some embodiments, the two girth hitch knots can be coupled to a single bone anchor 178. The single bone anchor 178 can be placed at the midline of the mandible (e.g., near the midline, substantially near the midline), as shown in FIG. 28. The single bone anchor 178 can be placed on either side (e.g., right side, left side) of the midline of the hyoid bone.

Figure 29C:
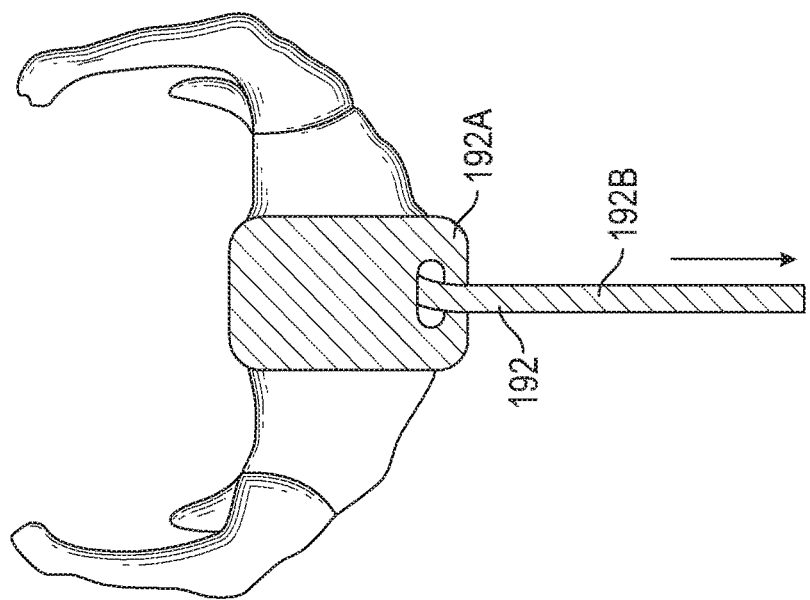
FIGS. 29A-29C illustrate an embodiment of an implant and a method of hyoid bone suspension.
Figure 29B:
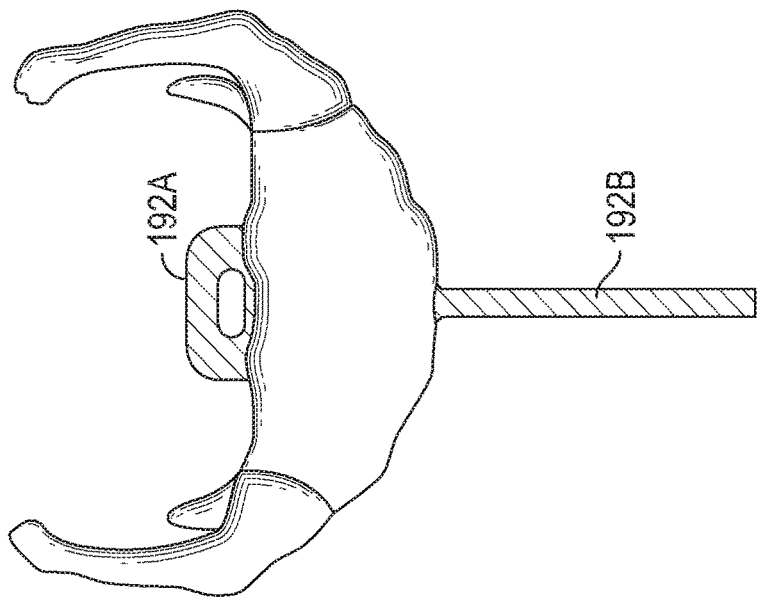
Figure 29A:
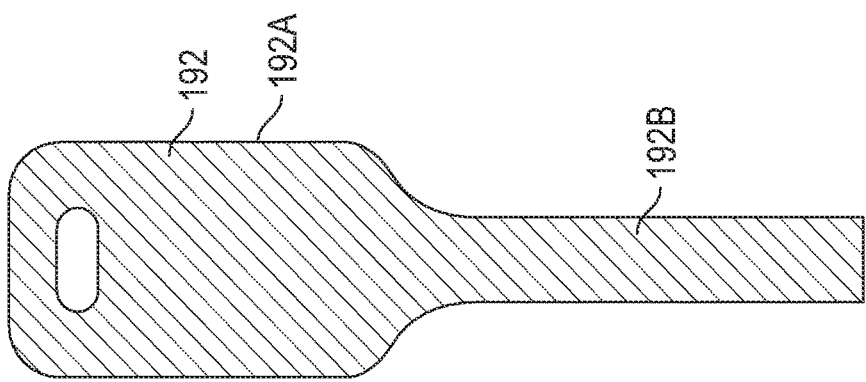

FIGS. 29A-29C illustrate an embodiment of a hyoid suspension implant 192 (e.g., an alternative to, or can be combined with the suture). FIG. 29A illustrates an implant 192. The implant 192 can include an implant head 192A, that can have a relatively larger width dimension, and a longitudinally extending tail 192B having a relatively smaller width dimension. The implant head 192A includes a slot or other feature designed to accept the longitudinally extending tail 192B. FIGS. 29B-29C show a method of using the implant 192. The implant 192 can be passed behind the hyoid bone. The implant head 192A is passed around the hyoid bone. The longitudinally extending tail 192B can be passed through the slot in the implant head 192A. The longitudinally extending tail 192B is tensioned. The implant 192 wraps around the hyoid bone, as shown in FIG. 29C. In some methods, the longitudinally extending tail 192B is passed around the hyoid bone. The longitudinally extending tail 192B can be passed through the slot in the implant head 192A. The longitudinally extending tail 192B can be tensioned. The implant 192 wraps around the hyoid bone, as shown in FIG. 29C.

Figure 30:
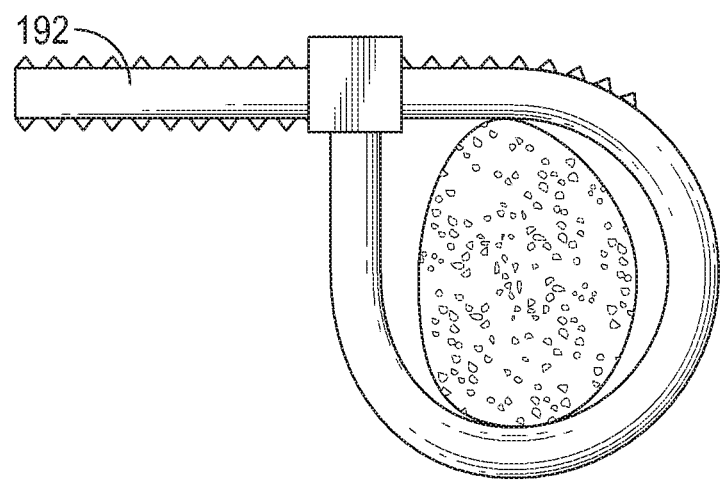
FIG. 30 illustrates an embodiment of an implant.

The implant head 192A, including the slot, and/or the longitudinal extending tail 192B can have additional features. The implant can include a locking mechanism. The locking mechanism can be a ratchet formed within or on the implant head 192A, the slot, and/or the longitudinal extending tail 192B. The locking mechanism can lock the implant 192 against the hyoid bone once the implant 192 has been tensioned. FIG. 30 shows an embodiment of the locking mechanism, surrounding a cross-section of a body structure, such as the hyoid bone. The longitudinally extending tail 192B includes teeth and/or ratchets that engage the slot. The slot includes teeth and/or ratchets that engage the longitudinally extending tail 192B. The locking mechanism locks the implant 192 in place after the implant 192 has been tensioned. The bone anchors 178 can also include teeth and/or ratchets that engage the longitudinally extending tail 192B. The longitudinally extending tail 192B can include teeth and/or ratchets that engage the bone anchor 178. The teeth and/or ratchet can provide a knotless method of locking the implant to the bone anchor.

The implant 192 can be manufactured from a biocompatible material (e.g., plastic). The implant 192 can be formed from any process (e.g., braiding suture). The teeth and/or ratchet can be formed into the implant (e.g., crimped into the suture). The teeth and/or ratchet can take any shape (e.g., balls, triangular teeth, and/or slits).

Figure 31:
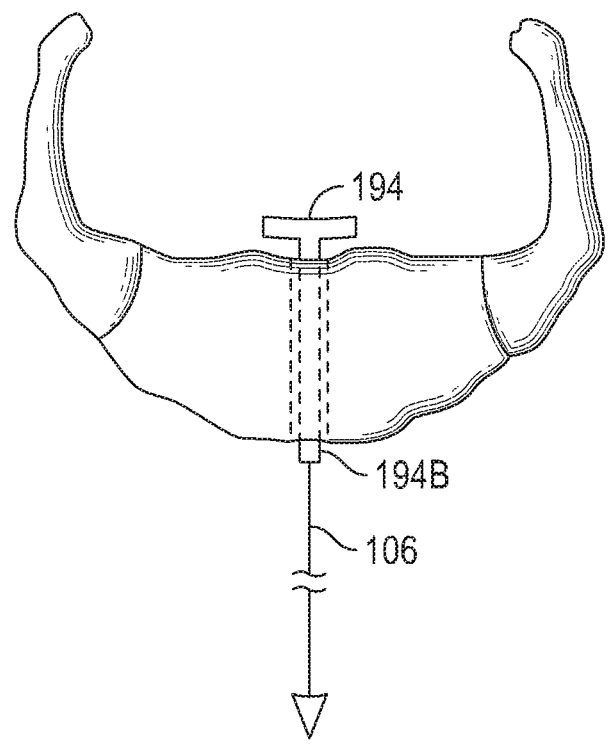
FIG. 31 illustrates a method of hyoid bone suspension using an implant.

FIG. 31 illustrates a method of attaching an implant to a hyoid bone. The method can include the step of drilling a small hole in the hyoid bone (e.g., a through hole). The implant 194 can be passed through the hole. The implant 194 can be reduced in diameter in order to fit through the small hole. The implant 194 can have a collapsed configuration and an expanded configuration. The implant 194 can be passed through the hole in the collapsed configuration. The implant 194 can be expanded to the expanded configuration after passing through the small hole. In the expanded configuration, the implant 194 cannot pass through the hole. For instance, the implant 194 can have a generally T-shaped configuration as shown in FIG. 31. The T-shape prevents the implant 194 from passing through the hole in the hyoid bone. A suture 106 (e.g., suture, suture tape) can be attached to the implant 194. The implant 194 can include a longitudinally extending tail 194B. The suture 106 can be coupled to the longitudinally extending tail 194B. The longitudinally extending tail 194B can be disposed within the hole. The suture 106 and/or longitudinally extending tail 194B can be connected to the bone or tissue (e.g., mandible, thyroid cartilage).

The implant 194 can be constructed from a material suitable for expanding (e.g., super elastic metal or plastic). The implant 194 can be constrained in the collapsed configuration, having a small diameter for delivery and/or insertion into the hole. The implant 194 can be constrained by a sheath. The implant 194 is allowed to expand once delivered and/or once the restraint is removed. The expanded configuration has a larger diameter than the collapsed configuration.

Figure 32A:
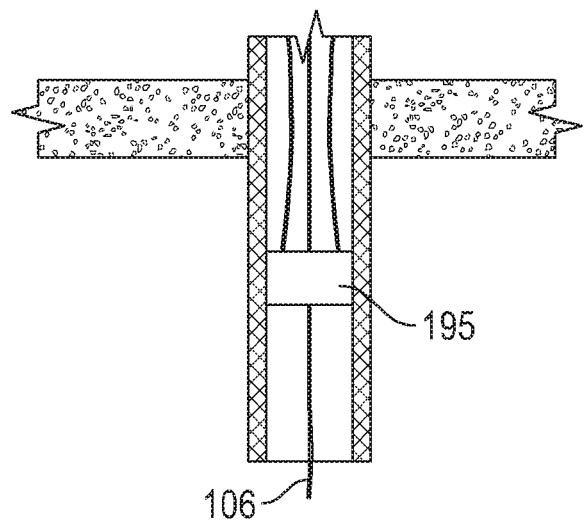
FIGS. 32A-32B illustrate an embodiment of an implant.
Figure 32B:
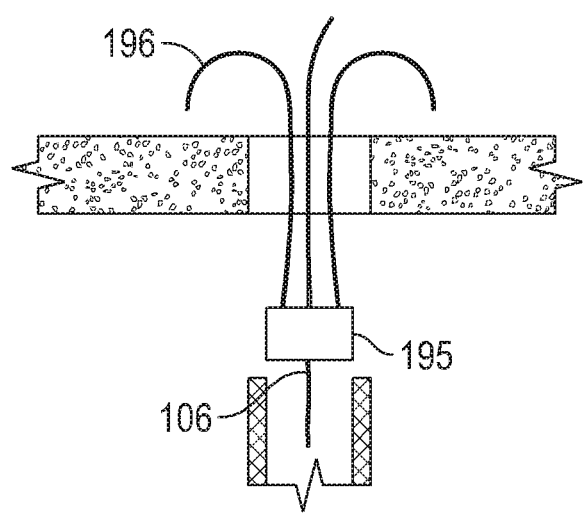

FIGS. 32A-32B illustrates a method of attaching an implant to a hyoid bone. The method can include the step of drilling a small hole in the hyoid bone (e.g., a through hole). The implant 195 can be passed through the hole. The implant 195 can have a reduced diameter configuration in order to fit through the small hole. The implant 195 can have a collapsed configuration and an expanded configuration. The implant 195 can be passed through the hole in the collapsed configuration. The implant 195 can be expanded to the expanded configuration after passing through the small hole. In the expanded configuration, the implant 195 cannot pass through the hole. FIGS. 32A-32B illustrate an embodiment of the implant 195. The implant 195 can include barbs 196. For instance, the barbs 196 can have a generally J-shaped configuration as shown in FIG. 32B. The J-shape prevents the implant 195 from passing through the hole in the hyoid bone. The barbs 196 can be formed from a material suitable for expanding (e.g., super elastic metal or plastic). FIG. 32A shows the barbs 196 in the collapsed configuration. The barbs 196 can be constrained by a sheath. The barbs 196 can be constrained by the small hole. The implant 195 can be coupled to a suture 106. FIG. 32B shows the barbs 196 in the expanded configuration. The sheath has been removed. The barbs 196 can have a larger diameter preventing the barbs 196 from passing back through the small hole.

Figure 33A:
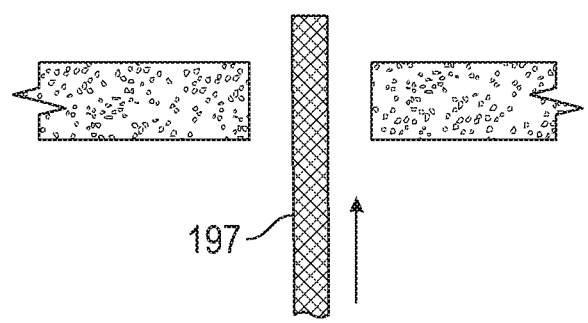
FIGS. 33A-33B illustrate an embodiment of an implant.
Figure 33B:
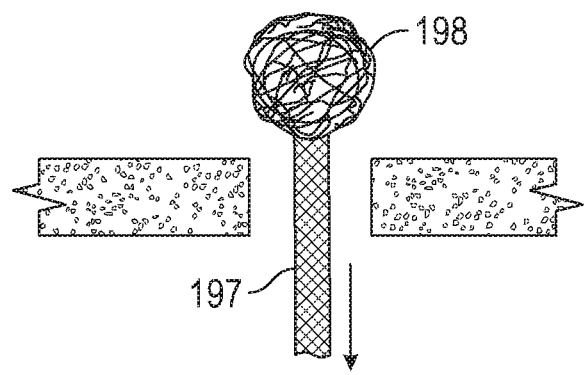

FIG. 33A-33B illustrates a method of attaching an implant to a hyoid bone. The method can include the step of drilling a small hole in the hyoid bone (e.g., a through hole). The implant 197 can be passed through the hole. The implant 197 can be reduced in diameter in order to fit through the small hole. The implant 197 can have a collapsed configuration and an expanded configuration. The implant 197 can be passed through the hole in the collapsed configuration. The implant 197 can be expanded to the expanded configuration after passing through the small hole. In the expanded configuration, the implant 197 cannot pass through the hole. FIGS. 33A-33B illustrate an embodiment of the implant 197. The implant 197 can include a suture 198. The implant 197 can have a collapsed configuration wherein the suture 198 extends along a longitudinal axis. The implant 197 can have an expanded configuration wherein the suture 198 forms a suture ball. FIG. 33A shows the implant 197 in the collapsed configuration. The suture 198 can be constrained by a sheath. The suture 198 can be constrained by the small hole. FIG. 33B shows the implant 197 in the expanded configuration. The suture 198 can have a larger diameter preventing the implant 197 from passing back through the small hole. The implant 197 can be coupled to suture 106. The implant 197 and/or the suture 106 may be coupled to a bone or tissue (e.g., mandible).

FIGS. 34A-34F illustrate an embodiment of a suture passer 200. The suture passer 200 can include a first section 202. The first section 202 can include a first handle 204. The first section can include a first tip 206. The first section 202 can be coupled to a second section 208. The first section 202 can be joined with, for example, a pivot pin to the second section 208 akin to a scissors tool. The second section 208 can include a second handle 210. The second section 208 can include a second tip 212.

The first tip 206 can form a jaw. The second tip 212 can form a jaw. The jaw can be curved. The jaw can include serrations or other features to improve grip to the bone or other tissue. The curvature of the jaw can allow the first tip 206 to surround a portion of a body structure, such as the hyoid bone. In some embodiments, the first tip 206 surrounds approximately 180 degrees of the hyoid bone. In some embodiments, the first tip 206 surrounds greater than 180 degree of the hyoid bone, approximately 270 degrees of the hyoid bone, greater than 270 degrees of the hyoid bone, etc. The curvature of the jaw can allow the second tip 212 to surround a portion of the hyoid bone. In some embodiments, the second tip 212 surrounds approximately 180 degrees of the hyoid bone. In some embodiments, the second tip 212 surrounds greater than 180 degree of the hyoid bone, approximately 270 degrees of the hyoid bone, greater than 270 degrees of the hyoid bone, etc. The first tip 206 and the second tip 212 can surround the entire hyoid bone or a substantial portion thereof.

Figure 34A:
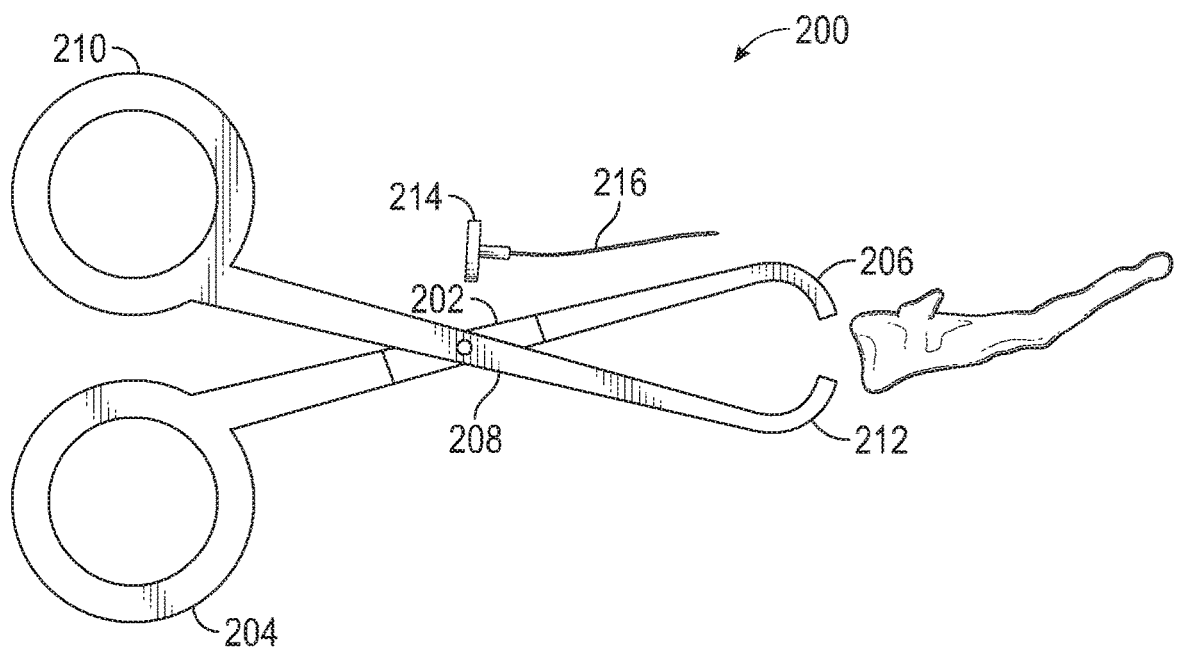
FIGS. 34A-34F illustrate an embodiment of a suture passer.
Figure 34B:
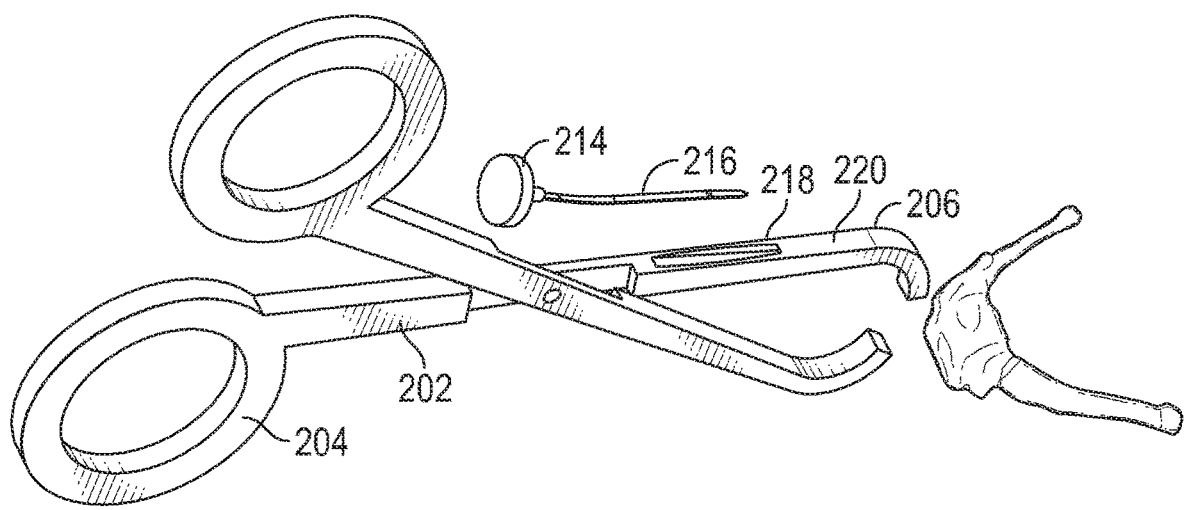

The assembly can include a plunger 216. The plunger 216 can include a head 214. The head 214 can have an enlarged cross-sectional area. The head 214 can guide the plunger 216. The plunger 216 can be flexible and/or elastic. As shown in FIG. 34B, the first section 202 can include a slot 218, either distal or proximal to the pivot. The slot 218 can be sized to accept the plunger 216. The slot 218 can be smaller than the diameter of the head 214 to limit the head 214 from passing through the slot 218. The slot 218 can be located on the opposite side of the pivot as the first handle 204. The slot 218 can be tapered. The slot 218 can extend from a surface 220 of the first section 202 to an interior lumen 222 of the first section 202 as described herein.

The plunger 216 can include a suture engagement mechanism. The suture engagement mechanism can be similar to the suture engagement mechanisms described herein for example with references to FIGS. 4A-4D. The suture engagement mechanism can include slots, holes, notches or lumens to engage the suture 106. The plunger 216 can engage the suture 106 to pass the suture 106.

Figure 34C:
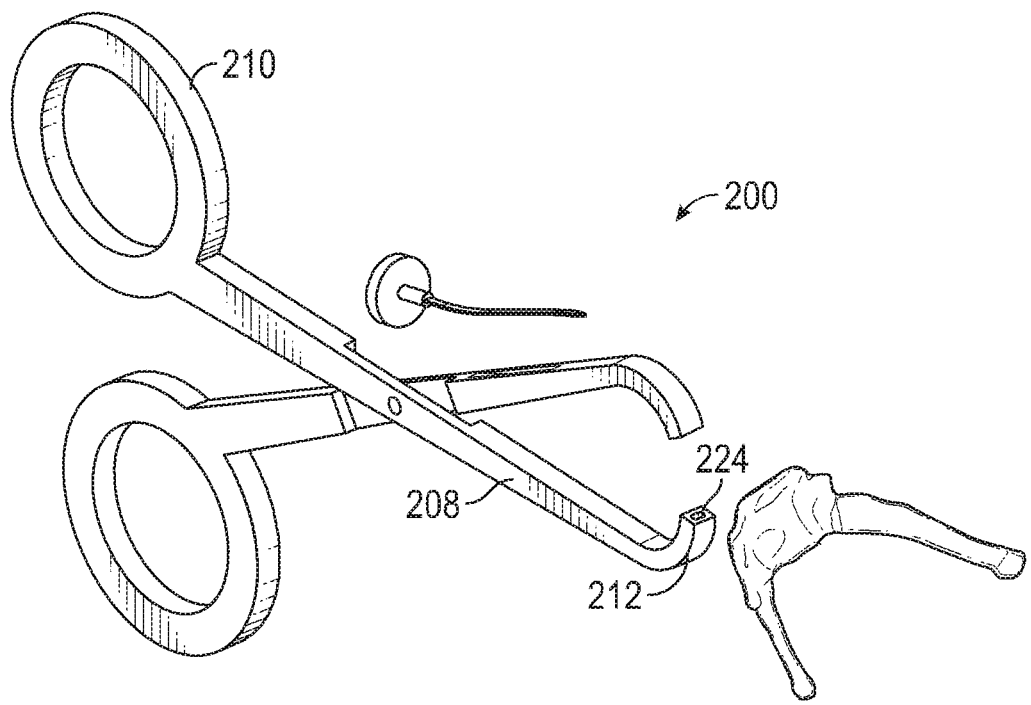

As shown in FIG. 34C, the second tip 212 can include an interior lumen 224. The interior lumen 224 can be sized to accept the plunger 216. In some embodiments, the second section 208 can include a slot (not shown). The slot on the second section 208 can be substantially similar to slot 218. The slot can be located on the opposite side of the pivot as the second handle 210. The slot on the second section 208 can be tapered. The slot on the second section 208 can extend from a surface of the second section 208 to the interior lumen 224 of the second section 202.

The interior lumen 222 of the first section 202 and the interior lumen 224 of the second section 202 can be aligned when the first tip 206 and the second tip 212 are brought together as shown in FIG. 34B. The interior lumens 222, 224 can form a continuous channel for the plunger 216 between the proximal slot opening on a sidewall and the distal-facing tip opening. The interior lumen 222 of the first section 202 is open at the first tip 206. The interior lumen 224 of the second section 208 is open at the second tip 212. This allows the plunger 216 to pass between the first section 202 and the second section 208.

Figure 34D:
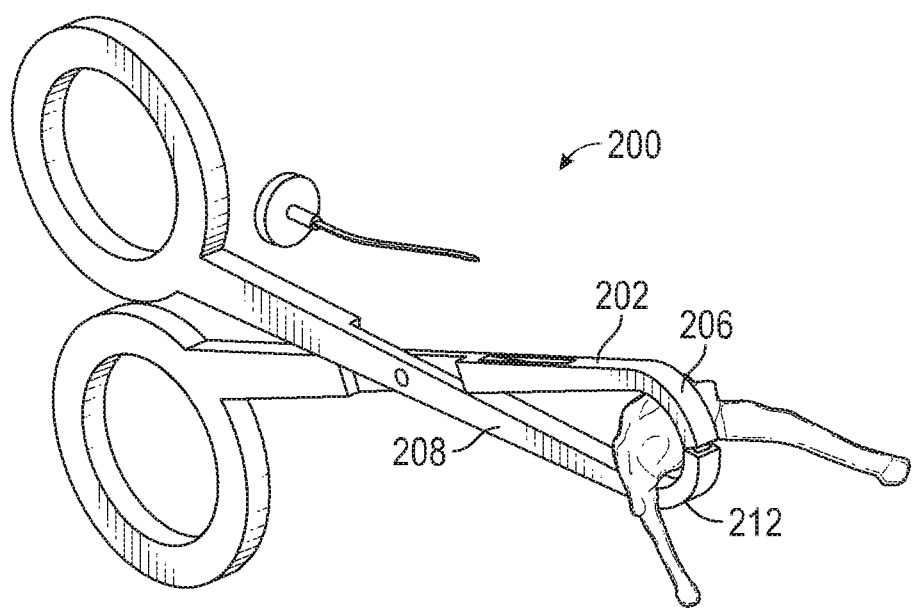

As shown in FIG. 34D, the suture passer 200 is advanced toward the hyoid bone. The suture passer 200 can be passed through a submental incision. The first tip 206 can be pivoted to surround the hyoid bone. The second tip 212 can be pivoted to surround the hyoid bone. The first tip 206 and the second tip 212 can be pivoted separately or simultaneously. The first tip 206 can be pivoted by actuating the handle 204. The second tip 212 can be actuated by pivoting the handle 210. The tips 206, 212 are brought toward each other. In some embodiments, the tips 206, 212 touch. In some embodiments, the tips 206, 212 are in close proximity. In some embodiments, a small gap is formed between the first tip 206 and the second tip 212. The interior lumen 222 of the first section 202 and the interior lumen 224 of the second section 208 are aligned when the tips 206, 212 are brought together. In some methods, the action of closing the tips 206, 212 stabilizes the suture passer 200 against the hyoid bone.

Figure 34E:
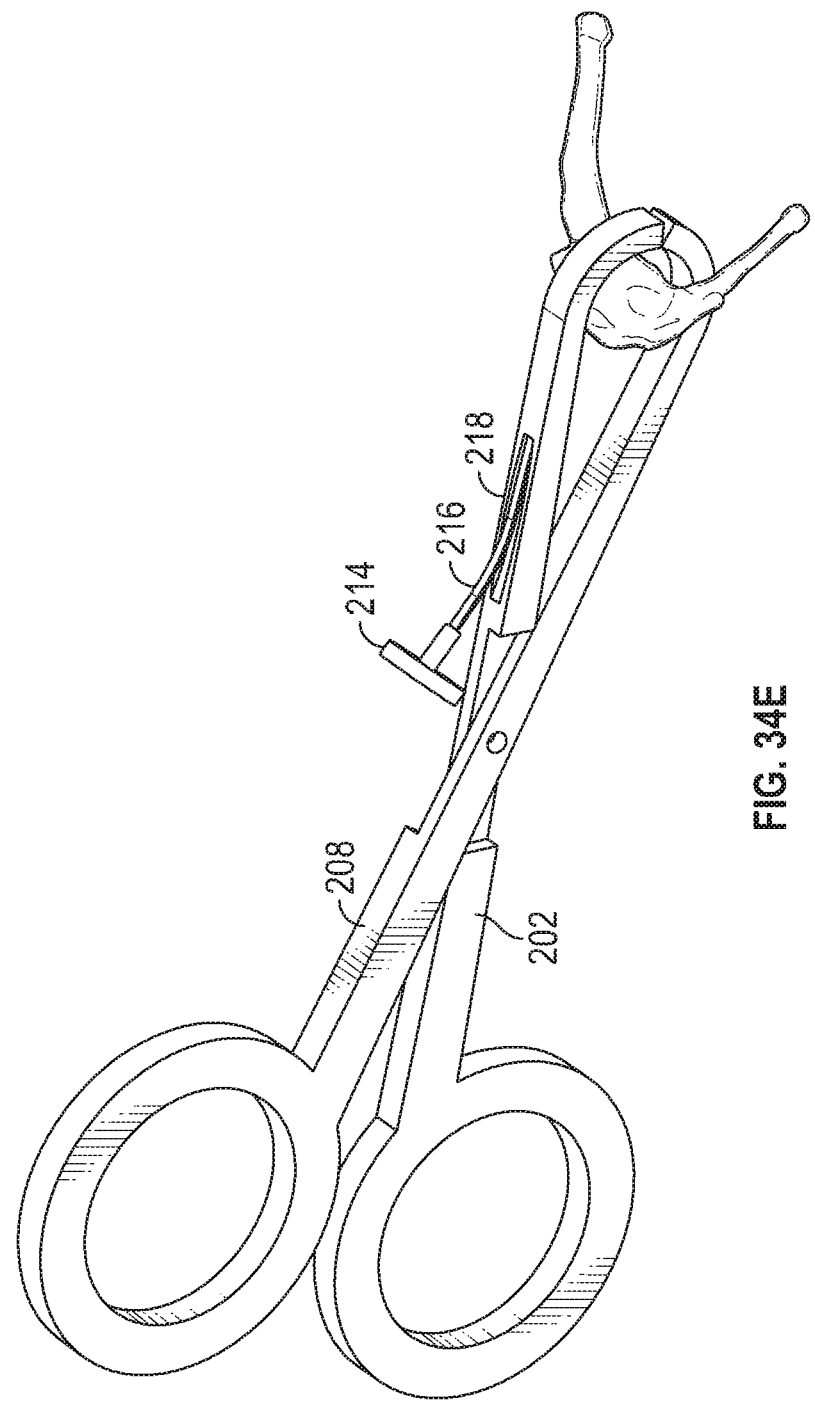

FIG. 34E shows that the plunger 216 can enter the slot 218 of the first section 202. The plunger 216 can be guided by the head 214. The plunger 216 can enter the interior lumen 222 of the first section 202. The plunger 216 can be advanced toward the interior lumen 224 of the second section 208. The plunger 216 can enter the interior lumen 224 of the second section 208. In some methods, the plunger 216 can exit the slot in the second section 208 (not shown). The head 214 can abut the surface 220 when the plunger 216 reaches the slot in the second section 208. The enlarged cross-section of the head 214 can prevent the head 214 from entering the slot 218. In other techniques, the plunger 216 enters the slot in the second section 208 and exits the slot 218 of the first section 202.

Figure 34F:
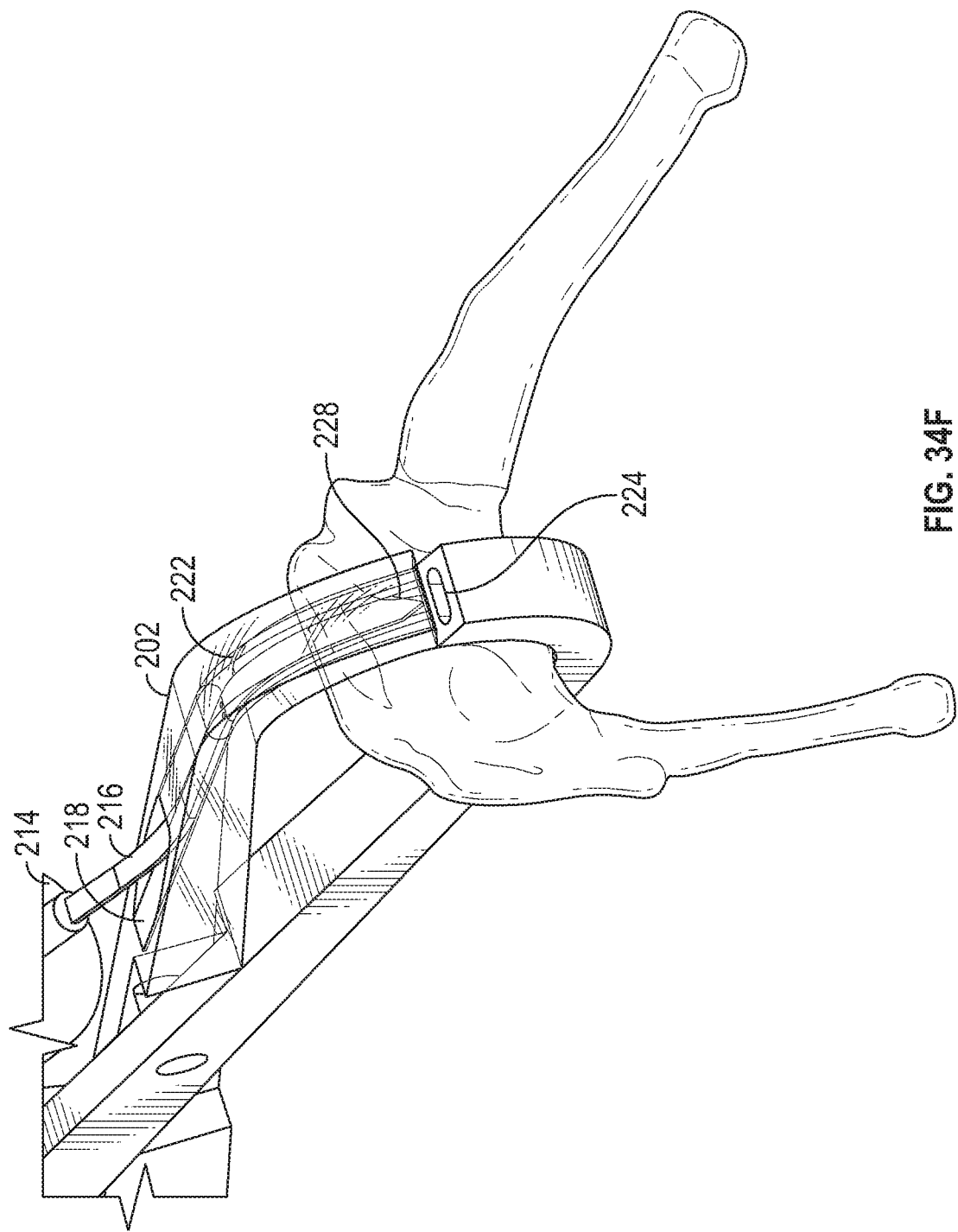

FIG. 34F show a cross-sectional view of the first section 202. The slot 218 can be tapered in some embodiments. The interior lumen 222 can align with the interior lumen 224. The interior lumens 222, 224 can be sized to accept the plunger 216. The plunger 216 can be advanced until it protrudes from the interior lumen 222. The plunger 216 can span the gap between the first tip 206 and the second tip 212. In other embodiments, the plunger 216 extends from the interior lumen 222 directly into the interior lumen 224. The plunger 216 can include a sharpened tip 228 to penetrate any tissue within the gap. The plunger 216 can bridge any potential gap between the first tip 206 and the second tip 212.

In some techniques, the second tip 212 can engage the suture 106 carried by the plunger 216. The second tip 212 can include a snare or other feature to engage the suture 106. The second tip 212 can unload the suture 106 from the plunger 216 as the plunger 216 is retracted. In some techniques, the plunger 216 is retracted with the first tip 206.

In some techniques, the second tip 212 engages the suture 106. The plunger 216 could include a snare or other feature to engage the suture 106. The plunger 216 can be advanced through the first tip 202 toward the suture 106. The plunger 216 would engage the suture 106 from the second tip 212. The plunger 216 can engage the suture 106 as the plunger 216 enters the interior lumen 224 of the second tip 212. The plunger 216 can be retracted to pull the suture 106 through the first tip 206.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "passing a suture to suspend the hyoid bone" include "instructing the passing of a suture to suspend the hyoid bone." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method comprising:
   providing a suture having a first strand, a second strand, and an arc between the first strand and the second strand;
   placing the arc on one side of a hyoid bone;
   placing the first strand and the second strand on the other side of the hyoid bone;
   forming a girth hitch around the hyoid bone;
   passing the first strand and the second strand through a bone anchor and adjusting tension of the suture by pulling the first strand and the second strand; and
   securing the first strand and the second strand to the bone anchor.

2. The method of claim 1, wherein the bone anchor is located on a mandible.

3. The method of claim 1, further comprising providing a second suture comprising a third strand, a fourth strand, and a second arc between the third strand and the fourth strand.

4. The method of claim 3, further comprising coupling the third strand and the fourth strand to a second bone anchor.

5. The method of claim 4, wherein the bone anchor is attached to a right side of a midline of a mandible and the second bone anchor is attached to a left side of the midline of the mandible.

6. The method of claim 3, further comprising forming a girth hitch around the hyoid bone with the second suture.

7. The method of claim 3, further comprising placing the second arc adjacent to the first arc on the hyoid bone.

8. The method of claim 3, further comprising pulling the second suture such that the second arc is on one side of the hyoid bone and both the third and fourth strands are on other side of the hyoid bone.

9. The method of claim 1, wherein providing a suture further comprises providing the suture with an elastomer surrounding a portion of the suture.

10. The method of claim 1, wherein providing a suture further comprises providing the suture with at least one bearing element on the suture.

11. The method of claim 10, wherein the at least one bearing element is at least partially covered by the elastomer.

12. The method of claim 1, wherein the bone anchor is attached to a mandible at a midline of the mandible.

13. The method of claim 1, wherein securing the first strand and the second strand to the bone anchor comprises tightening a screw.

14. The method of claim 1, wherein the suture is a large diameter suture, suspension loop, or suture tape.

15. A method of securing a hyoid bone, comprising:
providing a suture comprising a first segment, a second segment, and an arc between the first segment and the second segment;
placing the arc on one side of a hyoid bone;
placing the first segment and the second segment on the other side of the hyoid bone;
forming a girth hitch around the hyoid bone with the suture;
inserting the first segment and the second segment into a lumen of a bone anchor and adjusting tension of the suture; and
tightening a portion of the bone anchor to secure the first segment and the second segment.

16. The method of claim 15, wherein the bone anchor is located on a mandible.

17. The method of claim 15, further comprising providing a second suture comprising a third segment, a fourth segment, and a second arc between the third segment and the fourth segment and coupling the third segment and the fourth segment to a second bone anchor.

18. The method of claim 17, wherein the bone anchor is attached to a right side of a midline of a mandible and the second bone anchor is attached to a left side of the midline of the mandible.

19. The method of claim 15, wherein the suture is configured to be tightened and loosened without untying the girth hitch.

20. A method of securing a hyoid bone, comprising:
forming a girth hitch around a hyoid bone with a suture, wherein a first segment of the suture and a second segment of the suture pass under an arc of the suture;
inserting the first segment and the second segment into a passageway of a bone anchor;
pulling the first segment and the second segment through the passageway to adjust tension of the suture; and
securing the first segment and the second segment to the bone anchor after adjusting tension.

* * * * *